United States Patent [19]

Hirayama et al.

[11] Patent Number: 5,159,069
[45] Date of Patent: Oct. 27, 1992

[54] SULFATED TANNINS AND THEIR SALTS

[75] Inventors: Fukushi Hirayama, Tokyo; Keijiro Uchino, Kanagawa; Masaya Iwamoto, Kanagawa; Akira Fukuchi, Kanagawa; Masashi Hiramoto, Kanagawa; Hirokazu Yamamoto, Tokyo; Naoki Yamamoto; Hideki Nakashima, both of Yamaguchi; Shigenobu Kadota; Hiroshi Ogawara, both of Tokyo, all of Japan

[73] Assignees: Yamanouchi Pharmaceutical Co., Ltd.; NipponFlour Mills Co., Ltd., both of Tokyo, Japan

[21] Appl. No.: 450,912

[22] Filed: Dec. 14, 1989

[30] Foreign Application Priority Data

Dec. 20, 1988 [JP] Japan ................... 63-320947
May 16, 1989 [JP] Japan ................... 1-121700

[51] Int. Cl.$^5$ ............ A61K 31/70; C07H 11/00; C07C 305/00
[52] U.S. Cl. ................... 536/118; 558/26; 536/18.1; 536/18.2; 536/119
[58] Field of Search ........... 536/118, 21, 54; 514/23, 53, 54, 56, 25; 558/26

[56] References Cited

U.S. PATENT DOCUMENTS

| 4,465,666 | 8/1984 | Lukas et al. | 424/78 |
| 4,465,673 | 8/1984 | Tanaka et al. | 514/25 |
| 4,783,446 | 11/1988 | Neushul | 514/54 |

FOREIGN PATENT DOCUMENTS

| 0293826 | 12/1988 | European Pat. Off. . |
| 1326328 | 8/1963 | France . |
| 196884 | 3/1985 | Japan . |
| 142181 | 6/1987 | Japan . |
| 142193 | 6/1987 | Japan . |
| 88/00401 | 9/1988 | PCT Int'l Appl. . |
| 1439107 | 11/1988 | U.S.S.R. . |
| 239928 | 12/1988 | U.S.S.R. . |
| 88/06396 | 9/1988 | World Int. Prop. O. . |

OTHER PUBLICATIONS

Journal of Medicinal Plant Research—vol. 55, Apr. 1989, pp. 117-122—Okuda, et al.
Journal of Natural Products—Jul.-Aug. 1989, vol. 52, No. 4, pp. 762-768—Nishizawa, et al.
Effect of Tannins—Jul.-Aug., 1985, pp. 615-621—Kakiuchi, et al.

Primary Examiner—Johnnie R. Brown
Assistant Examiner—Everett White
Attorney, Agent, or Firm—Burgess, Ryan & Wayne

[57] ABSTRACT

Sulfated tannins or salts thereof are herein disclosed. These compounds can be prepared by a method which comprises reacting tannin with a sulfonating agent under a basic condition. These compounds show antiviral activity and reverse transcriptase inhibitor, effects and can be used to treat patients infected with a variety of virus such as AIDS virus, herpesvirus, influenza virus or rhinovirus.

9 Claims, 13 Drawing Sheets 3,4-DIGALLOYLQUINIC ACID-S

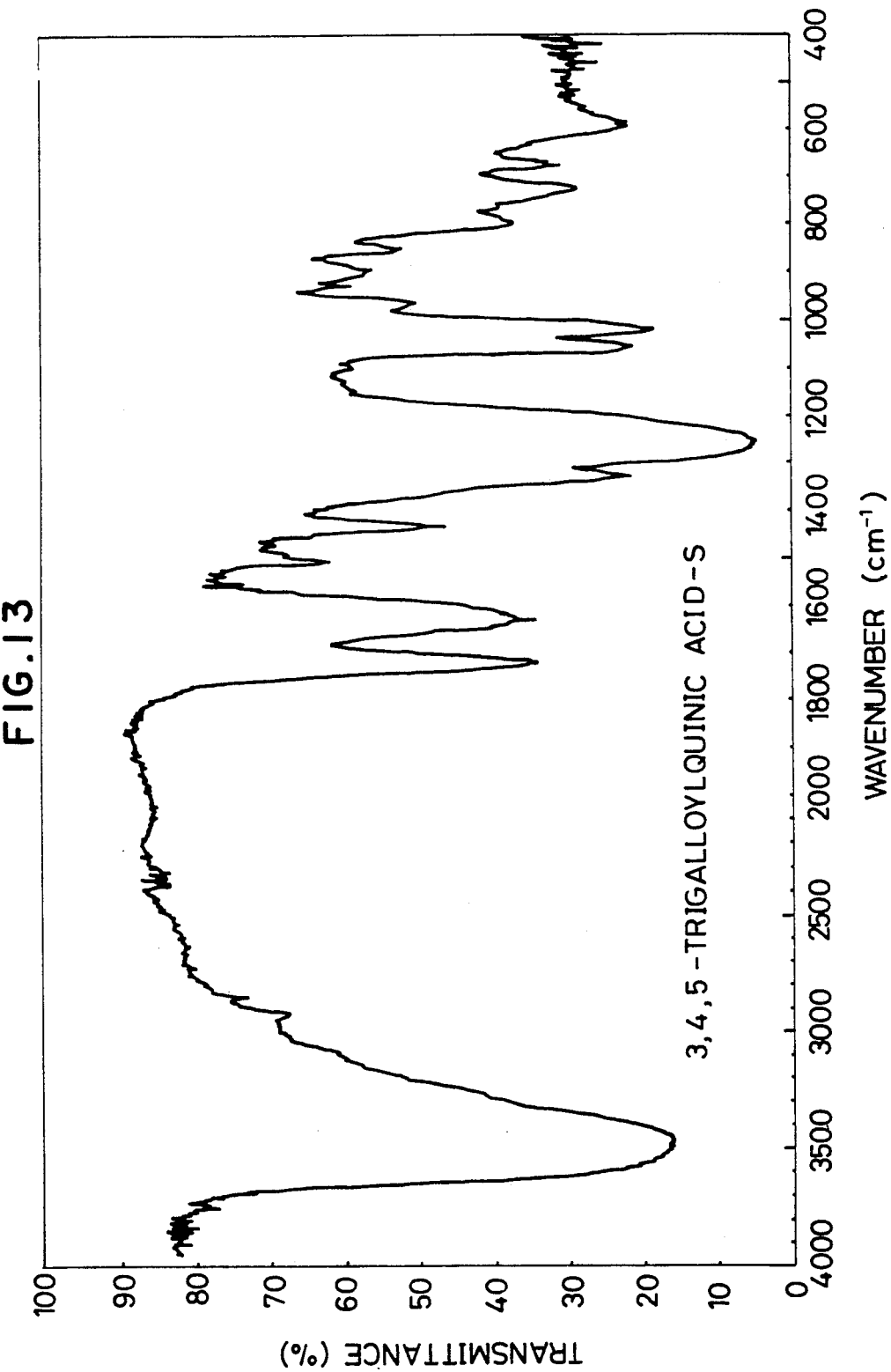

SULFATED TANNINS AND THEIR SALTS

BACKGROUND OF THE INVENTION

1. Field of the Invention

The present invention relates to novel sulfated tannins and their salts as well as an antiviral agent, in particular, that for retrovirus and a reverse transcriptase inhibitor.

2. Description of the Prior Art

Regarding viral infectious diseases, there has been desired to develop antiviral agents for use in their routine treatment. However, clinically effective ones have not yet been developed and hence the treatment thereof should in general rely on the symptomatic treatment. Recently, the development and investigation of antiviral agents for herpesvirus, those for AIDS (acquired immune deficiency syndrome) virus or the like have increased. Under such circumstances, the inventors of this invention have conducted studies to develop antiviral agents effective against AIDS virus and herpesvirus as well as other virus.

AIDS was reported for the first time in the United States in 1981 (see Gottlieb, M. S. et al., N. Engl. J. Med., 1981, 305, p. 1425; and Siegal, F. P. et al., N. Engl. J. Med., 1981, 305, p. 1439). Thereafter, the virus HIV (human immunodeficiency virus) which causes AIDS was identified in 1983 by Montagnier (France) (Barre-Sinoussi, F. et al., Science, 1983,220, p. 868) and then by Gallo (American) (Popovic, M. et al., Science, 1984, 224, p. 497).

It has been found, as a result of exploration of substances exhibiting infection-inhibitory effect, that azidothymidine (AZT) which is an analogue of nucleic acid (see Hiroaki Mitsuya et al., Proc. Natl. Acad. Sci. USA, 1985, 82, p. 7096; Hideki Nakajima et al., Antimicrob. Agents Chemother., 1986, 30, p. 933) and various kinds of dideoxynucleosides (see Hiroaki Mitsuya et al., Proc. Natl. Acad. Sci. USA, 1986, 83, p. 1911; Y. Hamamoto et al., Antimicrob. Agents Chemother., 1987, 31, p. 907) exhibit effect of apothanasia on the basis of in vivo studies and have been approved as an agent for treating AIDS.

However, patients suffering from AIDS must take AZT for a long period of time and thus various problems such as side-effects are still present.

In addition, Yamamoto et al. reported that the formation of multinucleated giant cells (Syncytium) could not be suppressed by simply employing AZT in a giant cell formation inhibitory experiment by co-cultivation of MOLT-4 and MOLT-4/HIV cells (see Hideki Nakashima, et al., Virology, 1987, 159, p. 169). It is thought that the formation of such giant cells plays an important role in the crisis of AIDS.

On the other hand, Nakashima and Yamamoto et al. have found that natural polysaccharides such as sulfated polysaccharides present in seaweeds and lentinan sulfate as well as other sulfated derivatives of polysaccharides (synthetic sulfated polysaccharides) have inhibitory effect on HIV infection (see Hideki Nakashima et al., Gann, 1987, 78, p. 1164).

Moreover, it is known that a certain kinds of polyphenols which are not sulfated show herpesvirus inhibitory effect and HIV inhibitory effect (Journal of Natural Products, 1989, vol. 52, No. 4, pp. 762–768).

For instance, there have been known herpesvirus inhibitory effect of (—)-epigallocatechin, procyanidine B2 3,3'-di-O-gallate and ratamenine belonging to condensed tannins (see Genichiro Nonaka et al., Collected Resume of 34th General Meeting of Japan Virus Society, 1986, Oct., p. 214) and HIV inhibitory effect of Agrimoniin, Coriariin A and Oanothein B belonging to hydrolyzable tannin (see Miyuki Asanaka, et al., Collected Resume of 1st Scientific Meeting of the Society for the Research on AIDS, 1987, Dec., p. 61). Further, it has been recently reported that a polyphenol type compound containing polysaccharides obtained by extracting pinecones of GOYO pine with hot water shows inhibitory effects on influenza virus, herpesvirus, hepatitis B virus and HIV (morning edition of the YOMIURI, Dec. 18, 1988).

SUMMARY OF THE INVENTION

Accordingly, an object of the present invention is to provide novel compounds showing antiviral effect.

Another object of the present invention is to provide novel compounds showing reverse transcriptase inhibitory effect.

A further object of the present invention is to provide a novel antiviral agent and a reverse transcriptase inhibitor containing the foregoing novel compound as an effective component.

The inventors of this invention have conducted investigation on whether sulfated tannins and their salts show HIV inhibitory effect or not. As a result, the inventors have found that these compounds show strong HIV inhibitory effect and thus have completed the present invention.

According to the present invention, there are provided novel sulfated tannins and their salts.

According to another aspect of the present invention, there are provided an antiviral agent and a reverse transcriptase inhibitor which comprise, as an effective component, at least one compound selected from the group consisting of sulfated tannins and salts thereof.

BRIEF EXPLANATION OF THE DRAWINGS

FIG. 13 is a chart of IR absorption spectrum of the compound obtained in Example 12.

DETAILED DESCRIPTION OF THE INVENTION

Figure 1:
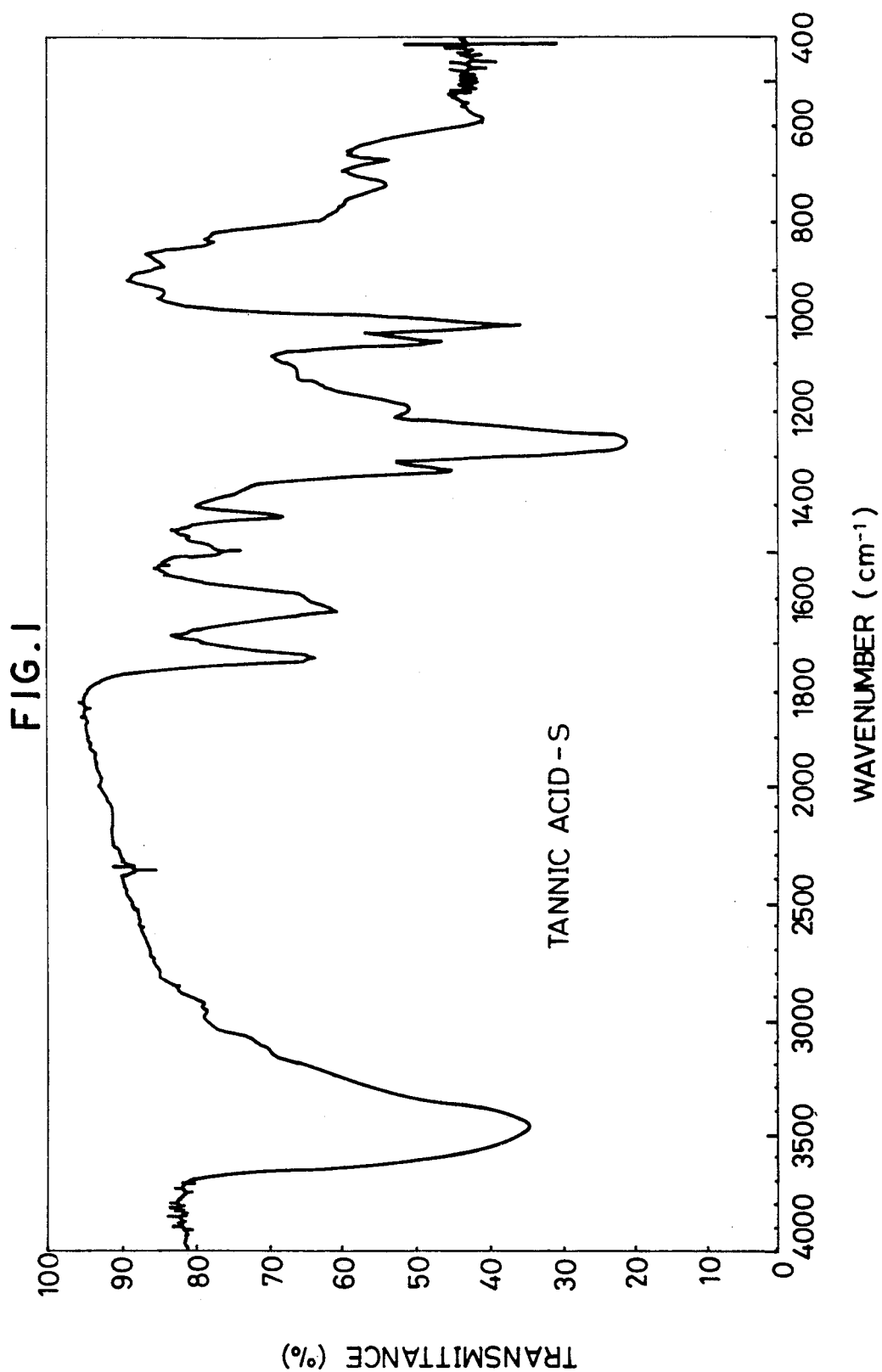
FIG. 1 shows a chart of IR absorption spectrum of tannic acid-S obtained in Example 1.

"Tannin" is a generic name of substances which are soluble in water, have a strong, rough taste and have an ability of tanning hides. In addition, it has a complicated structure based on a polyhydric phenol and is present extensively in plants. Tannins are roughly divided into two groups, i.e., hydrolyzable tannins and non-hydrolyzable tannins. The hydrolyzable tannins are hydrolyzed by heating with a dilute acid or treating with an enzyme tannase to give gallic acid, ellagic acid, or further complex polyphenol carboxylic acid and sugars or polyhydric alcohols. The non-hydrolyzable tannins do not provide hydrolyzates, but are converted into brownish substances called phlobaphene when they are heated together with a dilute acid. Therefore, they are called condensed tannins or phlobatannins.

The term "tannins" herein means hydrolyzable tannins, polyhydric phenols obtained by hydrolyzing the hydrolyzable tannins such as gallic acid, ellagic acid and complex polyphenol carboxylic acids and non-hydrolyzable tannins.

Specific examples of hydrolyzable tannins and polyhydric phenols obtained by hydrolyzing the hydrolyzable tannins used in the present invention are digallic acid, luteic acid, ellagic acid, chlorogenic acid, glucogallin, tetralin, hamamelitannin, nutgalls-tannin, tannic acid, geraniin, gallic acid, galloylgallic acid, ellagitannin, hexagalloylglucose, heptagalloylglucose, tetragalloylglucose, trigalloylglucose, pentagalloylglucose, digalloylquinic acid, trigalloylquinic acid and other hydrolyzable tannins having unknown structures. Preferred are tannic acid, ellagic acid, pentalgalloylglucose which is one of the components of the tannic acid, digalloylquinic acid and trigalloylquinic acid and in particular tannic acid, pentagalloylglucose, digalloylquinic acid and trigaloylquinic acid.

Tannic acid is a tannin derived from plants and in general prepared from Chinese gall or nut gall. This is used as, for instance, an ink, a dye or an antioxidant as well as a medicine such as a local astringent or a hemostat and is listed in Japanese Pharmacopoeia and U. S. Pharmacopoeia. Although tannic acid has long been used, its structure has not yet been well-defined and hence it varies depending on articles. For instance, Shoji Tomoda, "Shokubutsu Yakuhin Kagaku (Plant Pharmaceutical Chemistry)", 1982, p. 93, Published by Hirokawa Publishing Company discloses that the structural formula of the principal component of tannic acid is as follows:

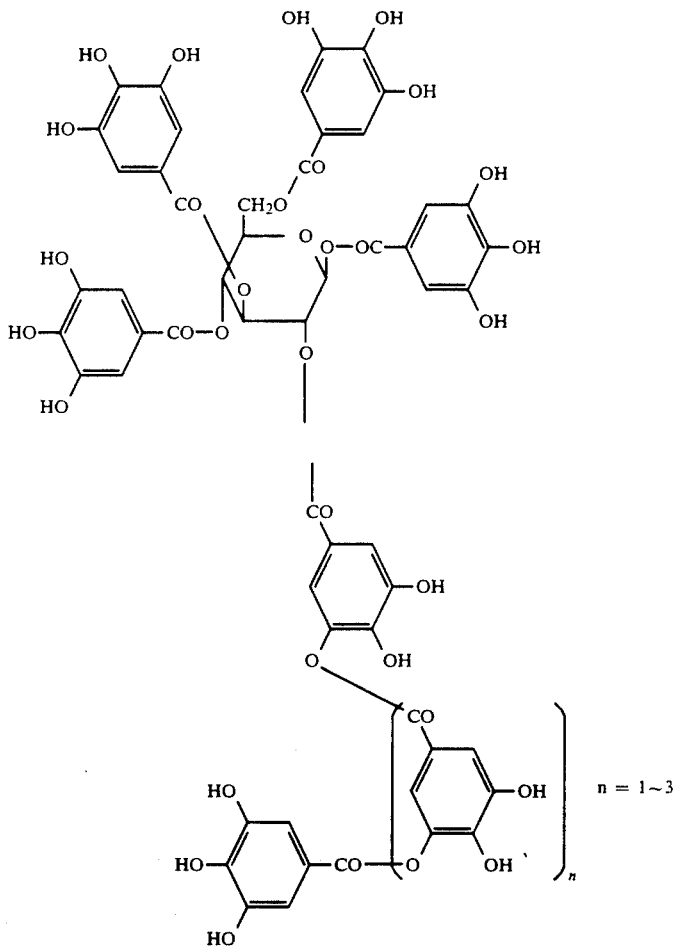

Japanese Pharmacopoeia (the Edition XI) discloses that tannic acid is in general a tannin obtained from Japanese gall or gall and that its history, methods for preparation and its structure are as follows:

History: Tannin was discovered, separated and named in 1793 by Deyeux and in 1795 by Sequin as an essential component present in gall. Thereafter, Berzelius prepared almost pure tannin and in 1834, Pelouze recognized that it is an acid. Its structure was studied by Nierenstein, Feist and then E. Fischer and his co-workers in 1912, but its correct structure has not yet been defined.

Method for Preparation: The method comprises pulverizing Japanese gall or gall, extracting with an ether · ethanol mixture (4:1), adding ⅓ volume of water to the exudate, mixing these with shaking to transfer tannic acid to water phase while transferring resins, dyes and the like to the ether phase, repeating this operation, combining the resulting water phases, evaporating the water phase under a reduced pressure, dissolving the residue in 8 volumes of water, decolorizing the water solution with active carbon, filtering the solution, removing impurities with ether, condensing the solution under a reduced pressure to obtain syrupy substance and then adding ethanol and ether to obtain foam-like substance to thus form an intended light material, or extruding the syrupy product through a small nozzle and drying to give needle-like product. During the preparation of this product, high temperature, alkalis and iron should not be employed. Chinese gall contains 65 to 75% of tannic acid, Japanese gall contains 60 to 68% tannic acid and gall contains 55 to 65% tannic acid.

Structure: The composition of tannic acid has not yet been well-defined, but 5 hydroxyl groups of glucose are bonded to free carboxyl groups of galloylgallic acid through ester bonds according to Fischer and Freudenberg:

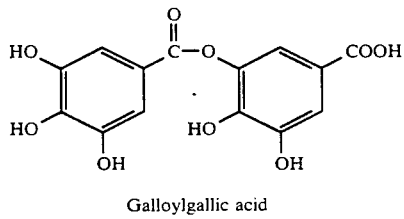

Galloylgallic acid

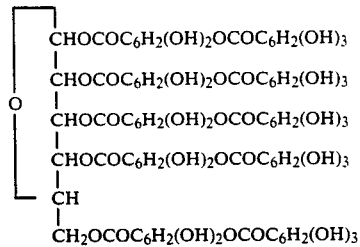

In U.S. Pharmacopoeia, there is a disclosure concerning tannic acid, but it does not disclose any structure thereof.

In Japan, various kinds of goods are put on the market. The HPLC (high performance liquid chromatography) elution patterns of products available from Wako Pure Chemicals Co., Ltd., and tannic acid according to Japanese Pharmacopoeia (available from Iwaki Pharmaceutical Co., Ltd. and Dainippon Pharmaceutical Co., Ltd.) approximately coincide with one another and, therefore, it is assumed that the compositions thereof also approximately coincide with each other. On the other hand, the HPLC elution patterns of these products do not coincide with that of tannic acid according to U.S. Pharmacopoeia and, therefore, it is considered that the compositions of the former differ from that of the latter.

As the non-hydrolyzable tannins usable in the present invention, there may be listed, for instance, catechin, epicatechin, epigallocatechin, epigallocatechin-3-gallic acid, gallocatechin, tannin of persimmon, theaflavin, flavan 3,4-diol, proanthocyan and other non-hydrolyzable tannins having unknown structures. Among these, preferred are epicatechin and epigallocatechin gallate.

The sulfation of tannins will now be explained in more detail below.

Tannins are converted into substances having high antiviral activity by sulfation. Furthermore, the sulfation makes it possible to improve solubility of tannin in water and to thus provide a stable aqueous solution. If an aqueous solution of tannin is allowed to stand for a long time, it is observed that precipitates are separated out and the solution causes browning. However, the sulfated tannins never suffer from such drawbacks.

In the present invention, the sulfur content of the sulfuric acid esters preferably ranges from 0.1 to 30% by weight and more preferably 5 to 20% by weight.

Any known sulfonating agents can be used in the sulfation, but preferably chlorosulfonic acid, sulfur trioxide, trimethylsilyl sulfonic acid chloride or the like are used from the viewpoint of reactivity and handling properties.

The reaction is preferably carried out under a basic condition. The reaction solvents are not critical and any solvents such as organic amines, dimethylsulfoxide and dioxane can be used, but preferred are organic amines such as pyridine, triethylamine and trimethylamine, which provide the desired basic condition by themselves. particularly preferred solvent is anhydrous pyridine.

The reaction may be carried out at room temperature, but from the viewpoint of organic chemistry, it is general to add the sulfonating agent under an ice-cooled condition and thereafter carry out the reaction at room temperature or with heating.

The amount of the sulfonating agent, for instance, chlorosulfonic acid exerts substantial influence on the degree of sulfation achieved. However, desired antiviral activity, stability and solubility of the resulting derivatives can certainly be expected even at a low degree of sulfation. In this connection, it is difficult to prepare products having various degree of sulfation and to separate and purify a product having a specific degree of sulfation. Therefore, it is desirable to use a large excess of the sulfonating agent to thus sulfate as high as possible.

The sulfur (S) content of the sulfated product thus obtained by using a large excess of the sulfonating agent ranges from 5 to 20% by weight and sulfated products having an almost the same sulfur content can be easily obtained in good reproducibility.

The reaction proceeds as soon as the sulfonating agent is dropwise added, but it is desirable to agitate at room temperature for a while. The sulfated products were sampled at 1, 24 and 48 hours after the initiation of the reaction, but the sulfur content of each product remained almost unchanged.

The resultant sulfated product may be isolated by any methods such as a method comprising subjecting the reaction mixture per se to desalting treatment and then isolating the sulfated product or a method comprising neutralizing the reaction mixture to thus recover the sulfated product as an alkali salt. Either of these may effectively be used, but it is preferred to recover the sulfated product in the form of a salt such as sodium salt or potassium salt. In addition, it is also preferred to remove pyridine which gives out a bad smell by extracting it with a non-hydrophilic solvent such as chloroform or ethyl acetate.

Alternatively, the foregoing procedures for sulfation may be repeated several times to obtain a sulfated product having a much higher degree of sulfation.

According to a preferred embodiment of the present invention, there is provided a sulfated pentagalloylglucose represented by the following general formula (I) or a salt thereof.

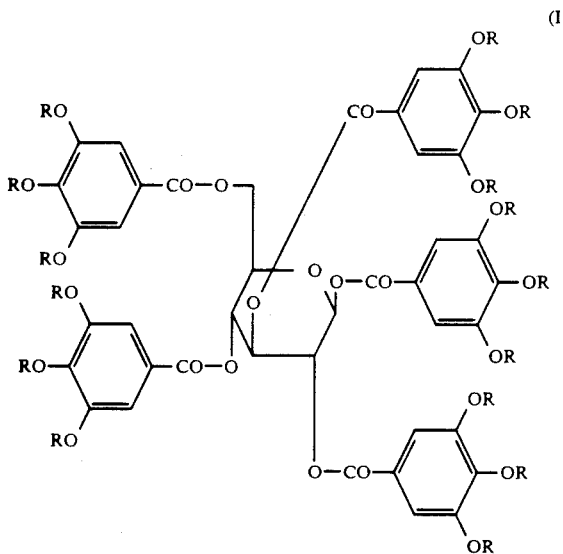

(in the formula (I), R represents —H or —$SO_3H$ provided that at least one R represents —$SO_3H$).

The galloyl group is a 3,4,5-trihydroxybenzoyl group represented by the following formula:

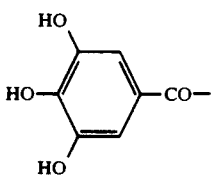

According to a preferred embodiment of the present invention, there are provided sulfated digalloylquinic acid or sulfated trigalloylquinic acid represented by the follow general formula (II) or salts thereof:

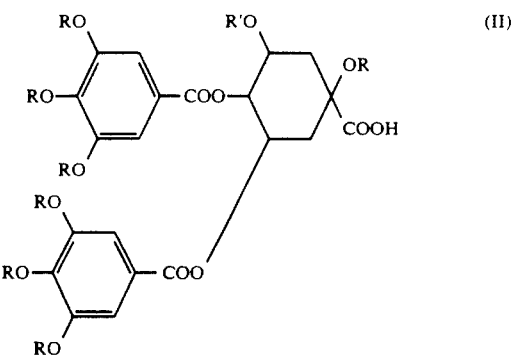

(in the formula (II), R' represents —H, —$SO_3H$ or a group represented by the following general formula:

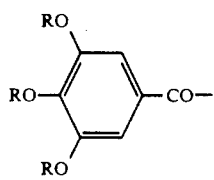

and R is —H or —$SO_3H$ provided that at least one of R is —$SO_3H$.)

The foregoing sulfated pentagalloylglucose, sulfated digalloylquinic acid or sulfated trigalloylquinic acid comprises a variety of sulfated products having different degree of sulfation. The compounds represented by the foregoing general formula (I) or (II) are those in which at least one hydroxyl group on the galloyl group is sulfated. In addition, sulfated galloyl groups in the formula (I) or (II) may be the same or different. The compounds represented by the general formula (I) or (II) preferably have an average degree of sulfation ranging from 10 to 70%. The compounds of the formula (I) or (II) may form salts. Examples of the salts are inorganic salts such as sodium salt and potassium salt.

The compounds represented by the general formula (I) or (II) may be prepared by sulfating pentagalloylglucose, digalloylquinic acid or trigalloylquinic acid. Such sulfation may be carried out in the same manner as used in sulfating phenolic hydroxyl groups as has been described above. More specifically, the sulfation can be performed by reacting pentagalloylglucose, digalloylquinic acid or trigalloylquinic acid with a sulfonating agent such as chlorosulfonic acid, sulfur trioxide or trimethylsilyl sulfonic acid chloride at room temperature or under cooling in a proper organic solvent. The reaction is preferably performed under a basic condition. Preferred examples of the reaction solvents are pyridine, triethylamine, trimethylamine, dimethylsulfoxide or dioxane. The degree of sulfation of the resultant product may be controlled by appropriately adjusting these sulfating conditions, in particular the amount of the sulfonating agent. For instance, if 300 eq., 20 eq. or 10 eq. of chlorosulfonic acid is reacted with pentagalloylglucose in pyridine under ice-cooling, intended product having a degree of sulfation of 60%, 47% or 40% can correspondingly be obtained. If it is desired to obtain product having a much higher degree of sulfation, the resultant product may additionally be sulfated.

After the reaction, the intended product can be isolated by neutralizing the reaction mixture and then extracting with a proper organic solvent, The resultant aqueous layer is dialyzed through a membrane filter to further purify it.

The antiviral agent and the anti-retroviral agent of the present invention comprise at least one compound selected from the group consisting of the foregoing sulfated tannins and salts thereof as an effective component.

(a) Method for Administration

The antiviral gent of the present invention may be orally and parenterally administered in the form of soft and hard capsules, tablets, granules, subtilized granules, powder for oral administration and in the form of injections, agents for instillation and other dosage forms such as suppositories which make it possible to maintain sustained absorption through mucous membrane in the form of a solid or suspended viscous liquid, for parenteral administration. The antiviral agent of the present invention may further be used in external administration methods such as administration in local tissues; intracutaneous, subcutaneous, intramuscular and intravenous injections; local painting, nebulization therapy, application as a suppository and vesicoclysis.

(b) Dose

The amount of the antiviral agent may be vary depending on various factors such as methods of administration and degree of malignancy of diseases; age, conditions of diseases and general conditions of patients; and degree of progress of diseases, but in general, the dose per day of the antiviral agent ranges from 0.5 to 5,000 mg for adults and 0.5 to 3,000 mg for infants expressed in the amount of the effective component.

(c) Method for Manufacturing Pharmaceutical Preparations

In the antiviral agent of the present invention, the amount of the effective component to be incorporated therein may widely vary depending on a specific dosage form, but in general the amount of the effective component to be incorporated into the drug desirably ranges from about 0.3 to 15.0% by weight for oral administration or for administration by absorption through mucous membrane and about 0.01 to 10% by weight for parenteral administration.

The antiviral agent containing the effective component of the present invention may be formed into aqueous solutions or oily preparations, in an ordinary manner, to obtain pharmaceutical preparations for subcutaneous and intravenous injection and alternatively, may be formed into dosage forms such as capsules, tablets and subtilized granules for use in oral administration.

In addition, for the purpose of imparting stability and acid resistance to the effective component to hence make the component withstand long term storage and to satisfactorily maintain its efficacy, the foregoing pharmaceutical preparations may be coated with pharmaceutically acceptable films to thus obtain antiviral agents exhibiting excellent stability.

Surfactants, excipients, lubricants, auxiliary agents and pharmaceutically acceptable film-forming substances used in manufacturing pharmaceutical preparations from the effective components of the present invention are as follows:

The antiviral agent of the present invention may comprise surfactants for improving disintegration and elution properties thereof and specific examples thereof are alcohols, esters, polyethylene glycol derivatives, fatty acid esters of sorbitan and sulfated fatty alcohols which may be used alone or in combination.

the antiviral agent of the present invention may also comprise excipients. Specific examples thereof include sucrose, lactose, starches, crystalline cellulose, mannitol, light anhydrous silicic acid, magnesium aluminate, magnesium metasilicate aluminate, synthetic aluminum silicate, calcium carbonate, sodium hydrogen carbonate. calcium hydrogen phosphate and calcium carboxymethyl cellulose which may be used alone or in combination.

As lubricants usable in the present invention, there may be mentioned, for instance, magnesium stearate, talc and hardened oils as well as mixture thereof. Moreover, the antiviral agent of the present invention may further comprise corrigents such as those for improving taste and odor thereof, for instance, common salt, sweetening agents, e.g., saccharin, sugar, mannitol, orange oil, glycyrrhiza extracts, citric acid, dextrose, menthol, eucalyptus oil and malic acid; perfumes, coloring agents and preservatives.

As auxiliary agents such as suspending agents and humectants, there may be mentioned, for instance, coconut oil, olive oil, sesame oil, peanut oil, calcium lactate, safflower oil and soybean phospholipid.

Specific examples of the film-forming substances are derivatives of carbohydrates such as cellulose and sugars, for instance, cellulose acetate phthalate (CAP); derivatives of polyvinyl compounds such as acrylic acid type copolymers and dibasic acid monoesters, for instance, methyl acrylate · methacrylic acid copolymers and methyl methacrylate · methacrylic acid copolymers.

It is also possible, in coating the pharmaceutical preparations with the foregoing film-forming substances, to add, to the film-forming substance, a coating aid such as a plasticizer and various additives for preventing mutual adhesion between the pharmaceutical substances during coating operation for the purpose of improving the properties of the film-forming substances and making the coating operations much easier.

The compounds of the present invention have reverse transcriptase inhibitory effect. Therefore, they are effective for use in making antiviral agents, in particular, anti-retroviral agents for treating and protecting from infectious diseases attributable to virus, in particular retrovirus such as HIV and adult T-cell leukemia virus. Besides retrovirus such as HIV, the compounds of the present invention are also effective to other common viruses such as herpesvirus, influenza virus and rhinovirus. In addition, the compounds of the present invention also show an effect for inhibiting the formation of giant cells caused by HIV, and, thus, the compounds are useful as drugs for treating various AIDS-related symptoms such as infectious diseases. Kaposi's sarcoma and pneumonyscarini pneumonitis.

In general, a single stranded or double stranded RNA is used in RNA virus as its genetic substance for the maintenance of its life. Among such RNA viruses, there is a group of viruses in which it is essential for its life cycle to synthesize complementory DNA from its RNA, therewith by means of reverse transcriptase (RTase). It is evidenced that the virus is integrated into genome of animal cells in the form of such a DNA.

It is considered that the compounds of the present invention can specifically inhibit RTase commonly existing in such virus to thus suppress the proliferation of the virus and the integration of the viral genome into those of the hose (animal cells).

The present invention will hereunder be described in more detail with reference to the following non-limitative working Examples, Reference Examples, Preparation Examples and Experiments.

EXAMPLE 1

Tannic acid (300 mg; available from Wako Pure Chemical Industries, Ltd.) was suspended in 45 ml of anhydrous pyridine, 11.4 g of chlorosulfonic acid (available from Nacalai Tesque Co., Ltd.) was added dropwise in small portions with ice-cooling and the mixture was stirred at room temperature for 2 days.

Then, 80 ml of water was added to the reaction mixture under ice-water cooling, followed by neutralizing it with a saturated sodium hydrogen carbonate aqueous solution and removing pyridine using the same volume of ethyl acetate. The aqueous layer was poured into a bag of a membrane filter having a fractional molecular weight of 1,000 (Spectra/pore 6; available from Spectrum Medical Industries Co., Ltd.) to perform dialysis against water for 7 days, the inner solution was lyophilized to thus obtain 323.4 mg of sodium salt of tannic acid sulfate (hereunder referred to as "tannic acid-S"). In the specification, a sodium salt of sulfated compound A is referred to as "A-S".

Physicochemical properties of tannic acid-S will be given below.
  (i) Appearance: powder of pale yellowish brown.
  (ii) Melting point: showing no clear melting point and decomposition point.
  (iii) Elemental Analysis: S: 13.0%
  (iv) IR absorption spectra (see attached FIG. 1): $\nu_{max}$ (KBr) cm$^{-1}$: 3448, 1731, 1634, 1505 1428, 1329, 1266, 1197 1054, 1021, 954, 897 845, 726, 673, 580.
  (V) Stability: stable in powder state and in the form of aqueous solution.

EXAMPLE 2

Figure 2:
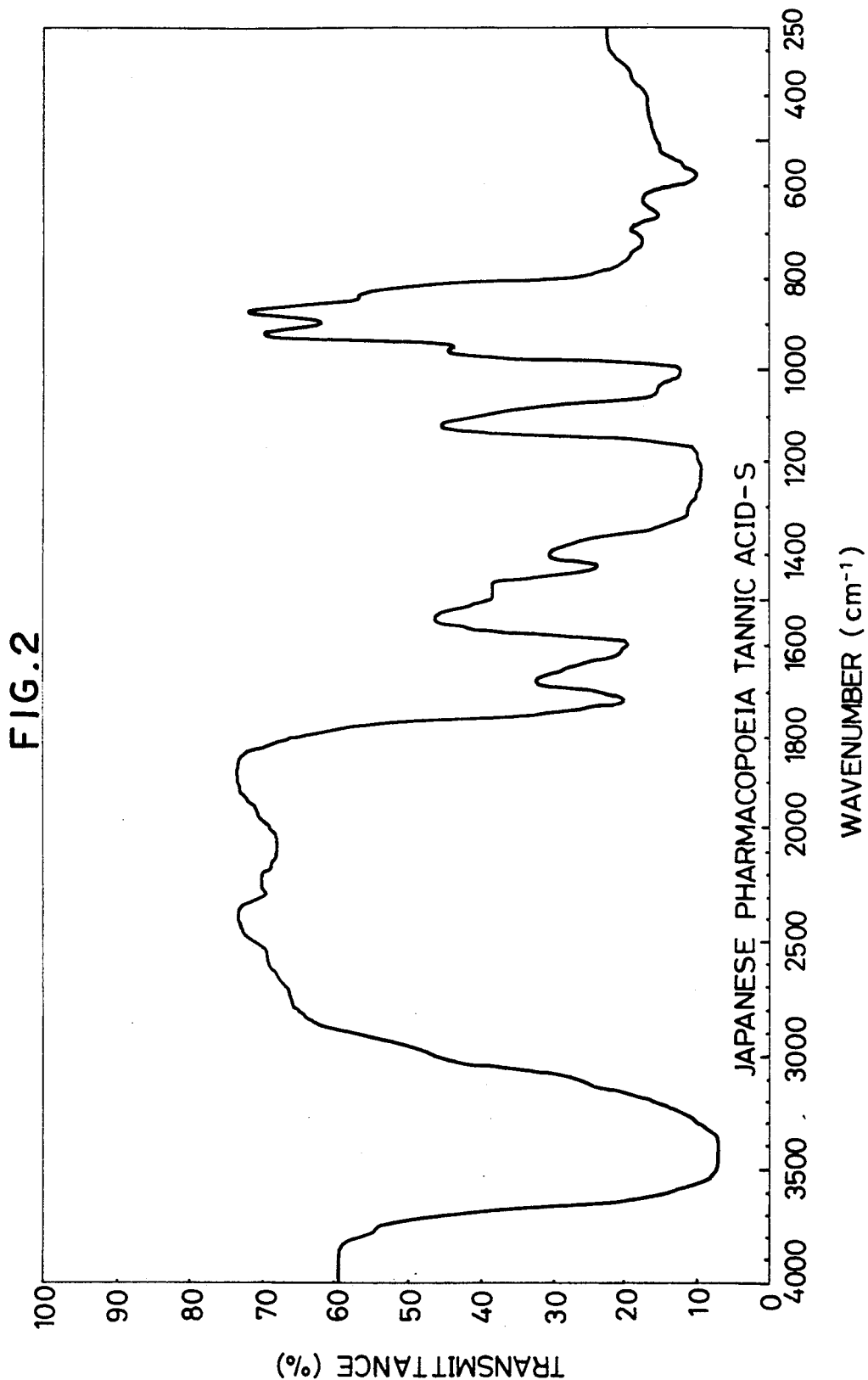
FIG. 2 is a chart of IR absorption spectrum of tannic acid-S (in accordance with the Japanese Pharmacopoeia) obtained in Example 2.

To a stirred mixture of 300 mg of tannic acid according to Japanese Pharmacopoeia (available from Iwaki Seiyaku Co., Ltd.) and 60 ml of anhydrous pyridine, there was dropwise added 11.4 g of chlorosulfonic acid slowly with ice-cooling and stirring. After the dropwise addition, the temperature of the reaction mixture was returned to room temperature and it was stirred for 24 hours. To the reaction solution, there was added 80 ml of water under ice-cooling, followed by neutralizing it with a saturated sodium bicarbonate aqueous solution and washing the solution twice with ethyl acetate. After concentrating the water phase, the reaction mixture was poured into a bag of a membrane filter having a fractional molecular weight of 1,000 (Spectra/pore 6; available from Spectrum Medical Industries Co., Ltd.) to perform dialysis against water for 7 days. The inner solution was again dialyzed through the same membrane filter against water for one day. Then, the inner solution was lyophilized to thus obtain 226 mg of sodium salt of sulfuric acid ester of tannic acid according to Japanese Pharmacopoeia (tannic acid-S).
  (i) Elemental Analysis: C 23.86%; H 1.94%; S 13.95%.
  (ii) IR absorption spectra (see attached FIG. 2): $\nu_{max}$ (KBr) cm$^{-1}$: 3420, 1720, 1625, 1600 1430, 1320, 1240, 1055 1010.
  (iii) UV absorption spectra: $\nu_{max}$ (H$_2$O) nm: 207, 256.

EXAMPLE 3

Figure 3:
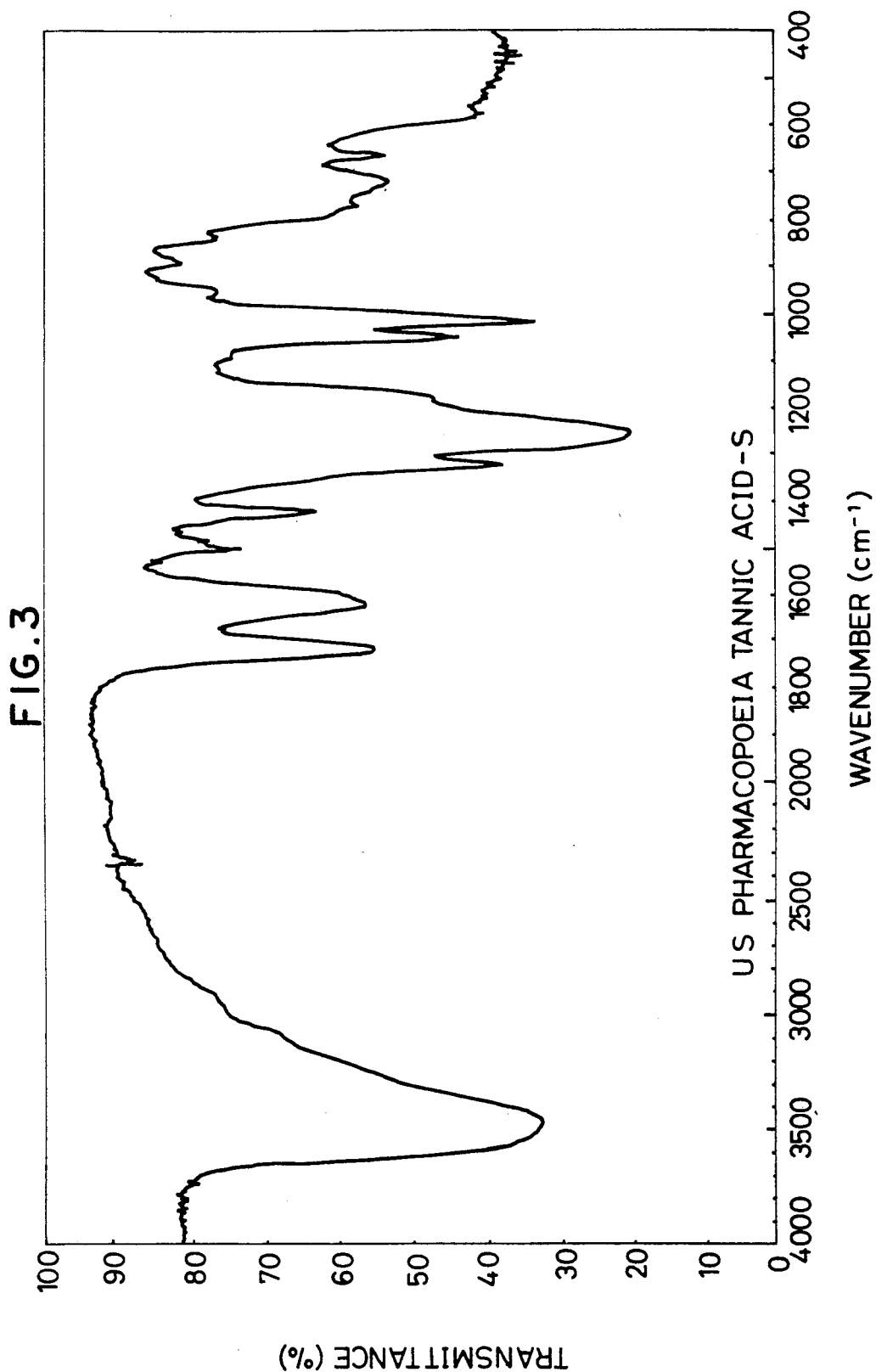
FIG. 3 shows a chart of IR absorption spectrum of tannic acid-S (in accordance with the U.S. Pharmacopoeia) obtained in Example 3.

To 1.5 g of tannic acid according to U.S. Pharmacopoeia, there was added 250 ml of anhydrous pyridine and the resulting mixture was sufficiently stirred under ice-cooling. Chlorosulfonic acid (57 g) was dropwise added slowly to the mixture and then the mixture was stirred at room temperature for 2 days. After adding 250 ml of water with ice-cooling, the mixture was neutralized with the addition of a saturated sodium hydrogen carbonate aqueous solution. This solution was extracted with ethyl acetate twice to remove pyridine. The water phase was poured into a bag of a membrane filter having a fractional molecular weight of 1,000 (Spectra/pore 6; available from Spectrum Medical Industries Co., Ltd.) to perform dialysis against water for 7 days. The inner solution was lyophilized to thus obtain 1.3772 g of sodium salt of sulfuric acid ester of tannic acid according to U.S. Pharmacopoeia (tannic acid-S).
  (i) Elemental Analysis: S 13.39%
  (ii) IR absorption spectra (see FIG. 3): $\nu_{max}$ (KBr) cm$^{-1}$: 3462, 1731, 1633, 1507, 1431, 1329 1260, 1055, 1021, 964, 900, 845 778, 729, 673.
  (iii) UV absorption spectra: $\lambda_{max}$ (H$_2$O) nm: 208, 257.

EXAMPLE 4

Figure 4:
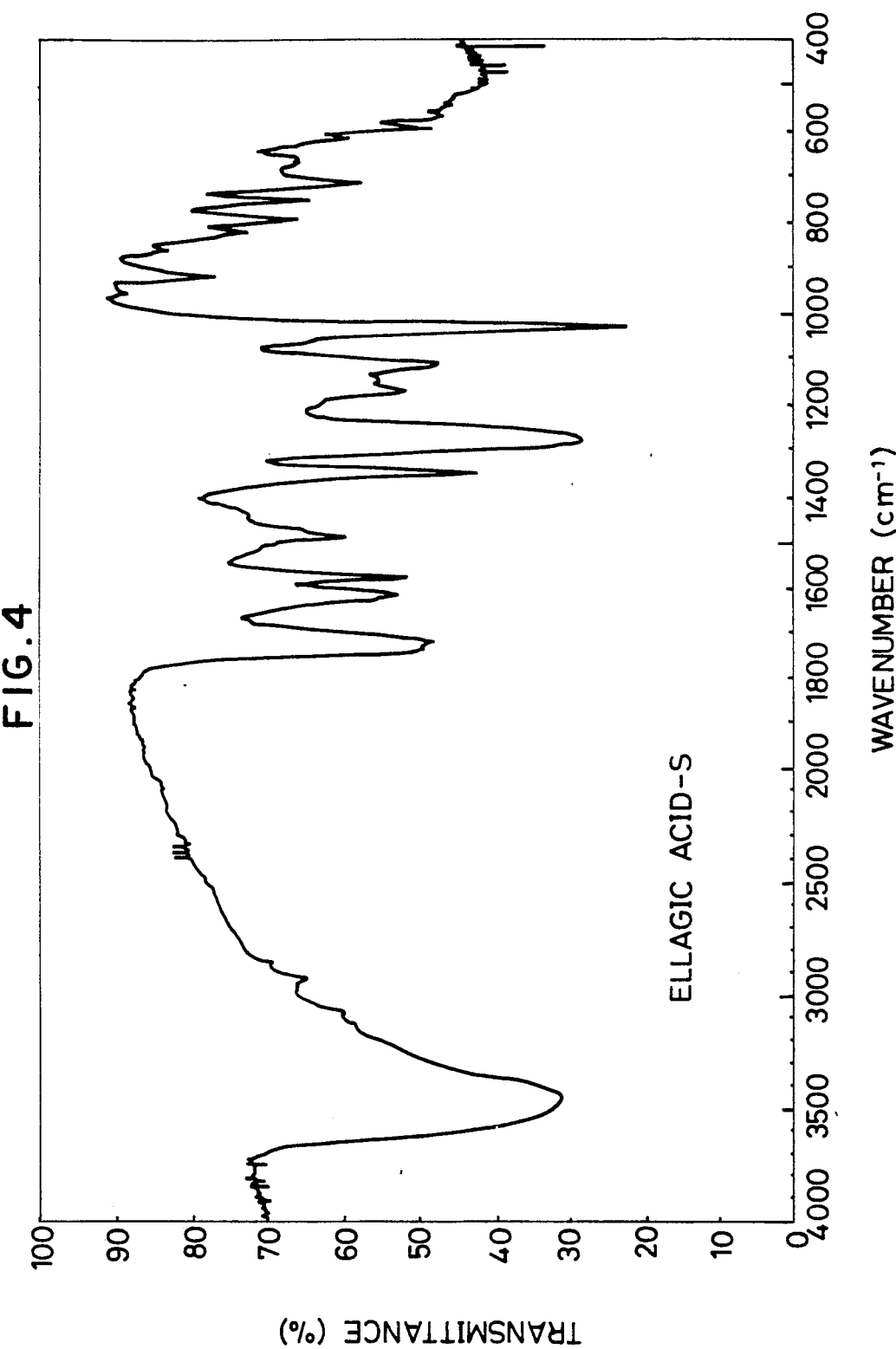
FIG. 4 is a chart of IR absorption spectrum of ellagic acid-S obtained in Example 4.

200 mg of ellagic acid (available from Tokyo Chemical Industries Co., Ltd.) was sulfated in the same manner as in Example 1 to thus obtain 76 mg of sodium salt of ellagic acid sulfate (ellagic acid-S). The sulfur content of the product was 12.0% (theoretical maximum thereof = 19.4%). The physicochemical properties of this ellagic acid-S are as follows:
  (i) Appearance: powder of pale yellowish brown.
  (ii) Elemental Analysis: C 28.29%; H 1.50%; S 12.0%.
  (iii) IR absorption spectra (see FIG. 4): $\nu_{max}$ (KBr) cm$^{-1}$: 3450, 1718, 1617, 1576, 1489, 1348 1280, 1172, 1113, 1034, 921, 824 793, 753, 715, 598.
  (iv) Stability: stable in powder state and in the form of aqueous solutions.

EXAMPLE 5

Figure 5:
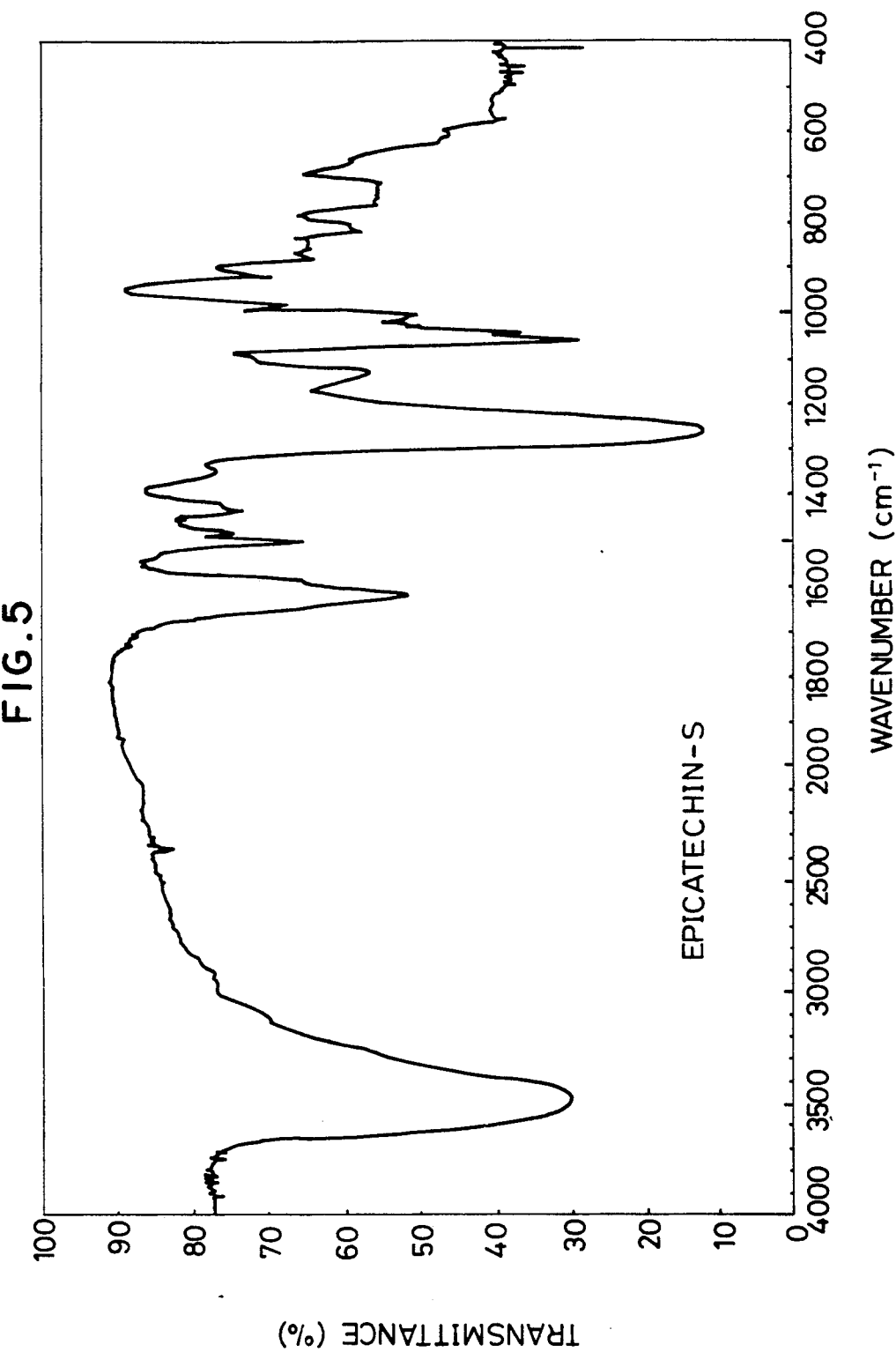
FIG. 5 is a chart of IR absorption spectrum of epicatechin-S obtained in Example 5.

(−)-Epicatechin (200 mg; available from Sigma Chemical Company) was sulfated in the same manner as used in Example 1 to thus obtain 62 mg of a sodium salt of epicatechin sulfate (hereunder referred to as "epicatechin-S"). The sulfur content of this product was 16.8% (theoretical maximum sulfur content = 20.0%). The physicochemical properties of epicatechin-S are as follows:
Epicatechin-S
  (i) Appearance: powder of pale yellowish brown.
  (ii) Elemental Analysis: C 20.05%; H 2.98%; S 16.8%.
  (iii) IR absorption spectra (see FIG. 5): $\nu_{max}$ (KBr) cm$^{-1}$: 3476, 1623, 1505, 1485, 1436, 1257 1132, 1062, 1045, 1031, 1006, 986 920, 878, 821.
  (iv) Stability: stable in powder state and in the form of aqueous solutions.

EXAMPLE 6

Figure 6:
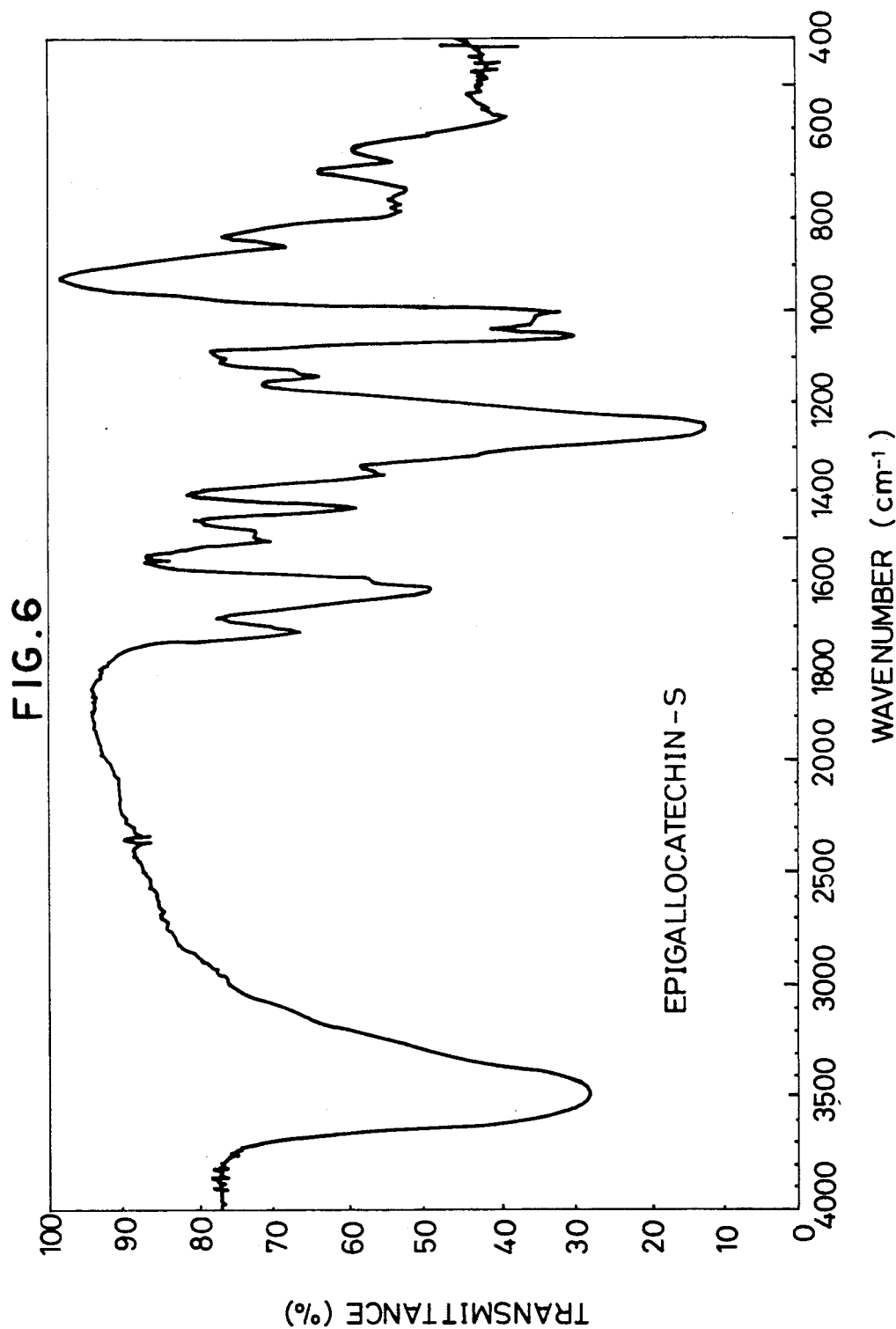
FIG. 6 is a chart of IR absorption spectrum of epigallocatechin gallate-S obtained in Example 6.

(−)-Epigallocatechin-3-gallate (100 mg; available from Wako Pure Chemical Industries Ltd.) was sulfated in the same manner as used in Example 1 to thus obtain 113 mg of sodium salt of sulfated (−)-epigallocathechin-3-gallate (epigallocatechin gallate-S). The sulfur content of this product was 15.3% (theoretical maximum sulfur content=20.1%). The physicochemical properties of epigallocatechin gallate-S are as follows:
(i) Appearance: powder of pale yellowish brown.
(ii) Elemental Analysis: C 21.08%; H 2.45%; S 15.3%.
(iii) IR absorption spectra (see FIG. 6): $\nu_{max}$ (KBr) cm$^{-1}$: 3470, 1715, 1621, 1506, 1488, 1436 1362, 1265, 1141, 1059, 1006, 858 780, 765, 730, 674, 580.
(iv) Stability: stable in powder state and in the form of aqueous solutions.

REFERENCE EXAMPLE 1

To 1 g of tannic acid according to Japanese Pharmacopoeia (available from Iwaki Seiyaku Co., Ltd.), there were added 50 ml of methanol and 25 ml of acetate buffer (pH 5.5) and the resultant mixture was stirred at 50° C. for 18 hours. After distilling off methanol under a reduced pressure, the residue was extracted three times with ethyl acetate and then the solvent was distilled off under a reduced pressure. This crude product was fractionated by HPLC (YMC-PACK, D-ODS-5 20×250 mm; eluent=methanol: tetrahydrofuran: phosphate buffer (pH 4.5)=3:1:7) to obtain 282 mg of 1,2,3,4,6-penta-O-galloyl-β-D-glucose.

FABMS (Neg): m/z 939 (M-H)$^-$.

$^1$H NMR: $\delta_{ppm}$ (500 MHz; acetone d$_6$) 4.46, 4.61, 5.67, 5.72, 6.06, 6.39, 7.04, 7.08, 7.12, 7.17, 7.24.

$^{13}$C NMR: $\delta_{ppm}$ (125 MHz, COM; acetone d$_6$) 63.43, 69.92, 72.35, 73.91, 74.52, 93.94, 110.78, 110.81, 110.92, 111.03, 120.50, 121.11, 121.12, 121.21, 121.98, 139.61, 139.74, 139.89, 139.94, 140.39, 146.40, 146.48, 146.51, 146.56, 146.67, 165.60, 166.25, 166.29, 166.53, 167.07.

Figure 7:
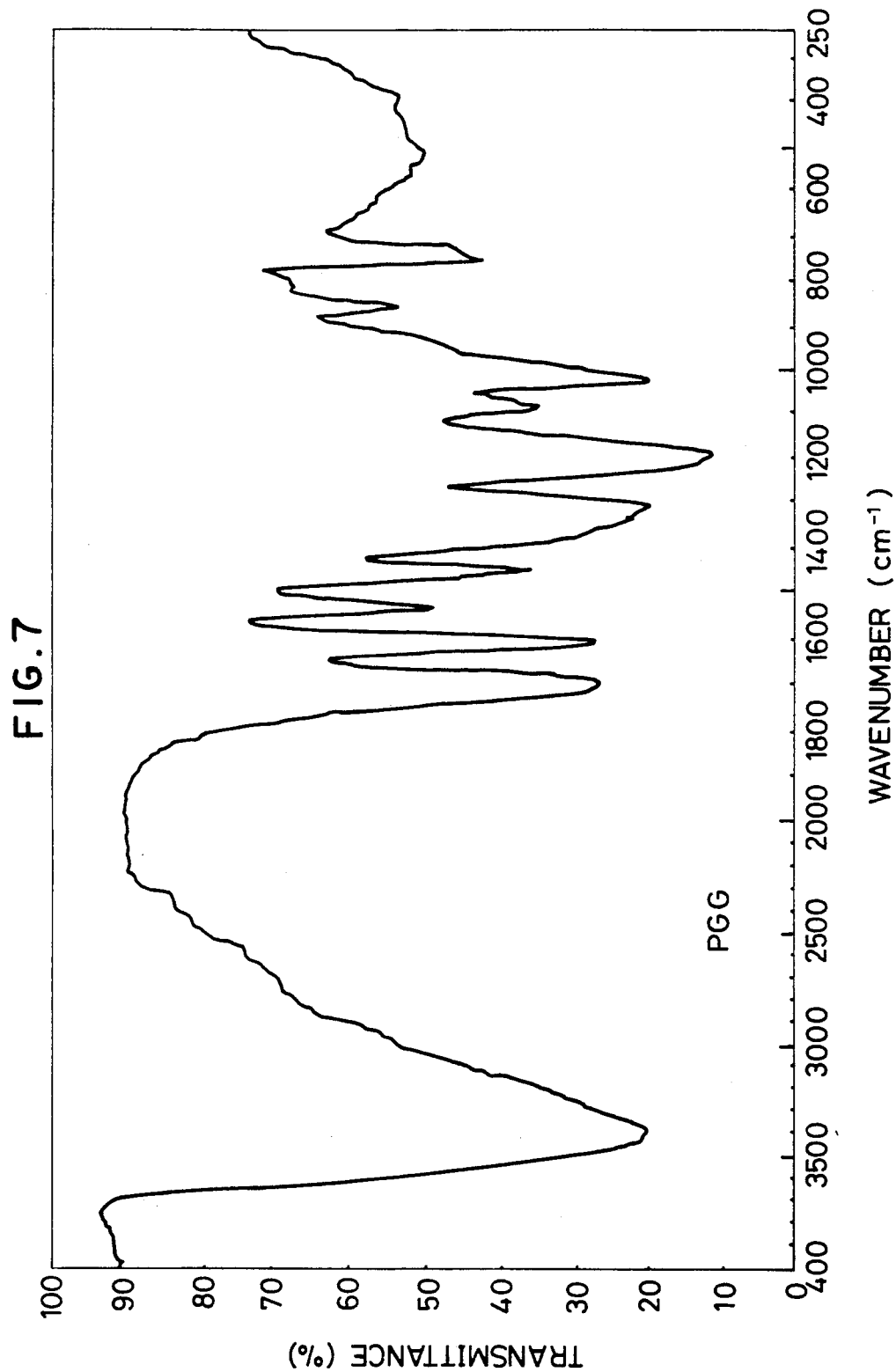
FIG. 7 is a chart of IR absorption spectrum of 1,2,3,4,6-penta-O-galloyl-$\beta$-D-glucose obtained in Reference Example.

IR: (see FIG. 7): $\nu_{max}$ (KBr) cm$^{-1}$: 3380, 1700, 1610, 1530, 1450, 1310, 1200, 1090, 1020, 870, 760.

UV: $\lambda_{max}$ (H$_2$O) nm: 212, 277.

M.P.: 190° C. (decomposed).

EXAMPLE 7

To 107 mg of 1,2,3,4,6-penta-O-galloyl-β-D-glucose, there was added 21 ml of anhydrous pyridine and the resultant mixture was sufficiently stirred in a nitrogen atmosphere with ice-cooling. To the mixture, there was dropwise added 4.1 g of chlorosulfonic acid slowly and then the mixture was stirred at room temperature for 12 hours. Water (5 ml) was added to the reaction mixture with ice-cooling, followed by neutralizing it with a saturated sodium hydrogen carbonate aqueous solution and extracting the mixture twice with ethyl acetate to remove pyridine. The resultant aqueous phase was concentrated and poured into a bag of a membrane filter having a fractional molecular weight of 1,000 (Spectra/pore 6; available from Spectrum Medical Industries Co., Ltd.) to perform dialysis against water for 7 days. The inner solution was lyophilized to thus obtain 131 mg of the sodium salt of sulfuric acid ester of 1,2,3,4,6-penta-O-galloyl-β-D-glucose (PGG-S).

Elemental Analysis: C 22.52; H 1.88; S 11.56 (%).

Figure 8:
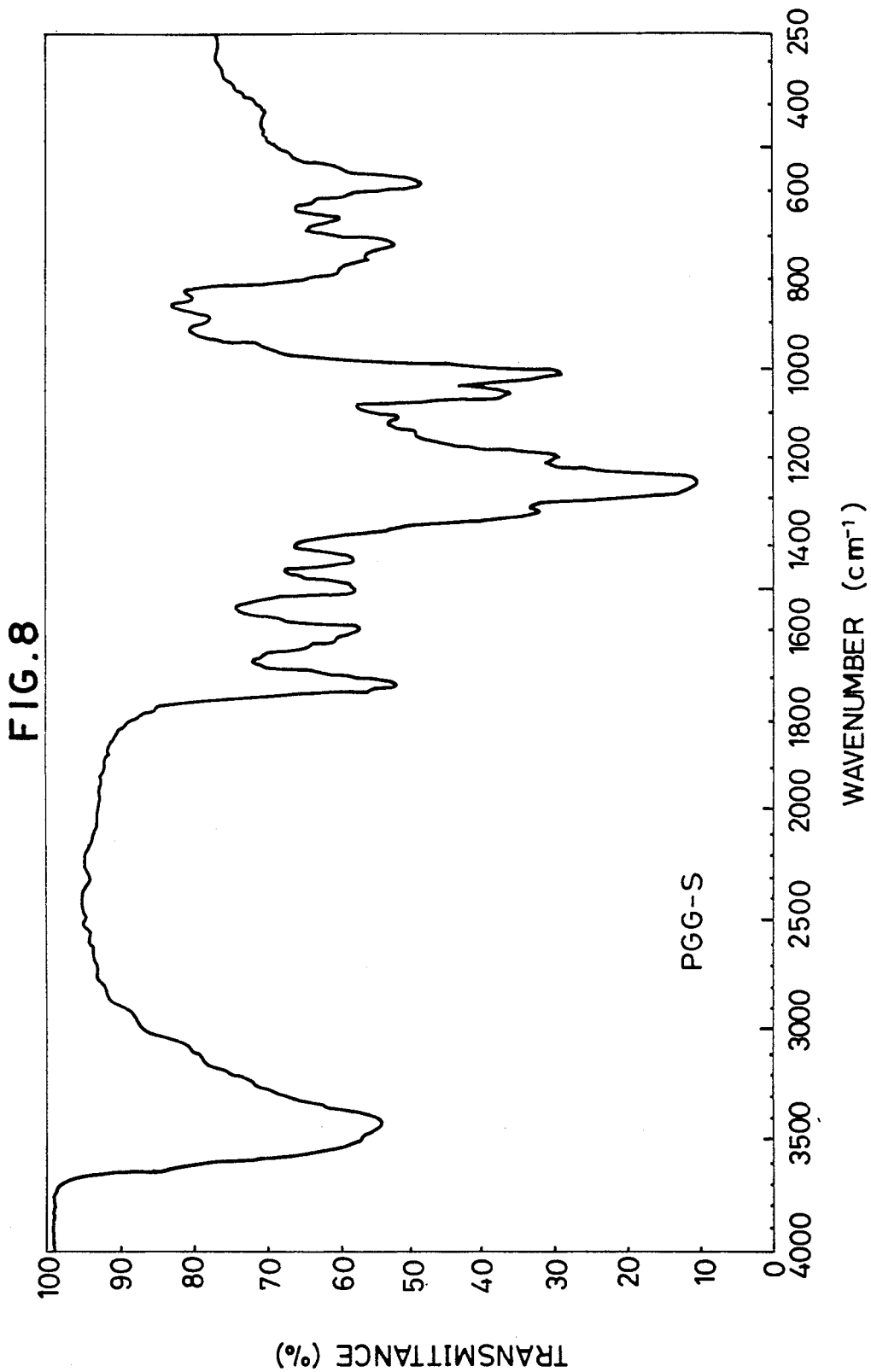
FIG. 8 is a chart of IR absorption spectrum of the compound obtained in Example 7.

IR: (see FIG. 8): $\nu_{max}$ (KBr) cm$^{-1}$: 3420, 1720, 1590, 1510, 1430, 1310 1260, 1200, 1050, 1010, 720, 670 590.

UV: $\lambda_{max}$ (H$_2$O) nm: 207, 255.

EXAMPLE 8

To 20 mg of 1,2,3,4,6-penta-O-galloyl-β-D-glucose, there was added 1 ml of anhydrous pyridine and the resultant mixture was sufficiently stirred in a nitrogen atmosphere with ice-cooling. To the mixture, there was dropwise added 54 mg of chlorosulfonic acid slowly and then the mixture was stirred at room temperature for 12 hours. Water (0.3 ml) was added with ice-cooling, followed by neutralizing it with a saturated sodium hydrogen carbonate aqueous solution and extracting the mixture twice with ethyl acetate to remove pyridine. The resultant water phase was poured into a bag of a membrane filter having a fractional molecular weight of 1,000 (Spectra/pore 6; available from Spectrum Medical Industries Co., Ltd.) to perform dialysis against water for 7 days. The inner solution was lyophilized to thus obtain 31 mg of the sodium salt of sulfuric acid ester of 1,2,3,4,6-penta-O-galloyl-β-D-glucose (PGG-S).

Elemental Analysis: C 24.40; H 3.17; S 9.03 (%).

Figure 9:
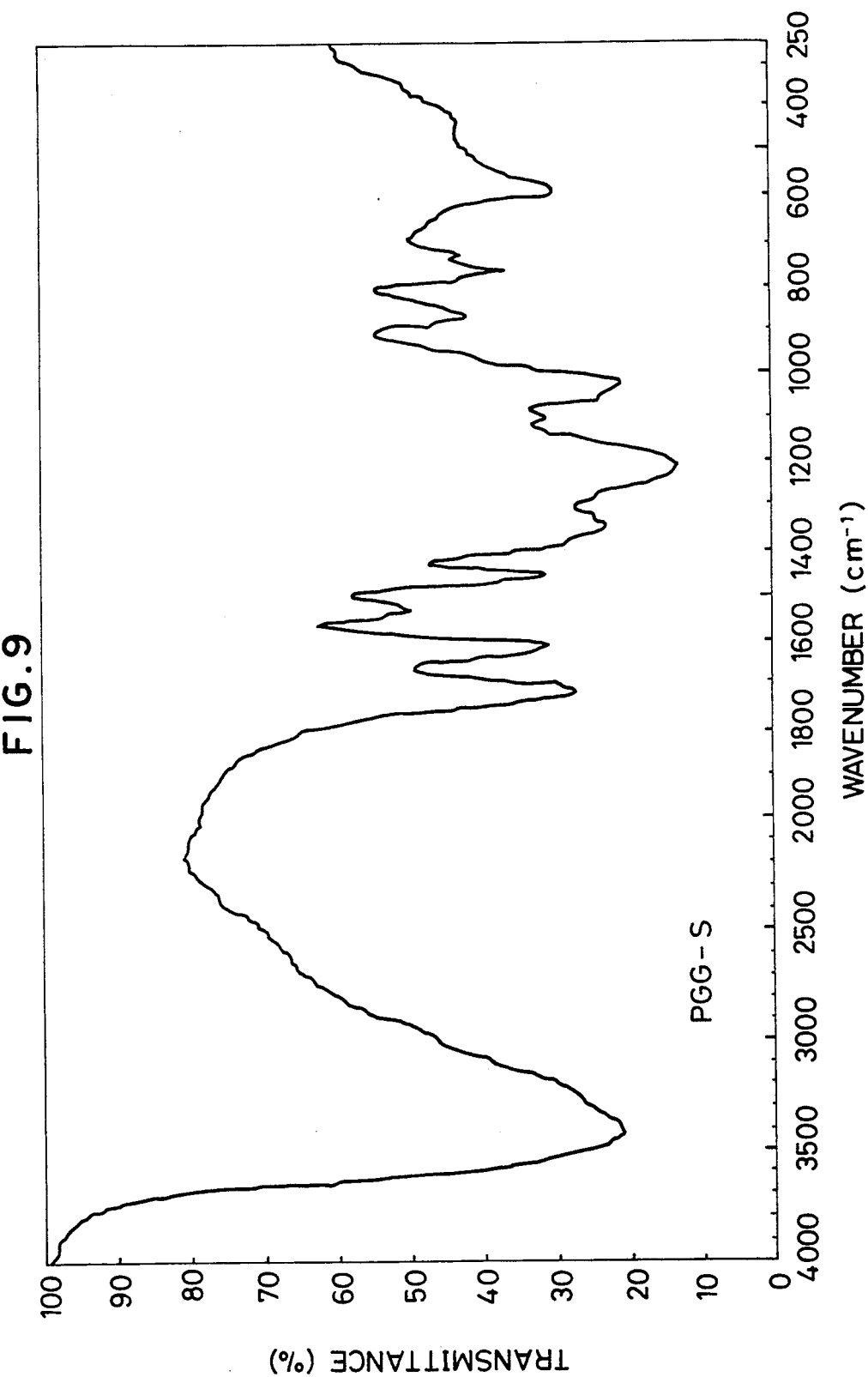
FIG. 9 is a chart of IR absorption spectrum of the compound obtained in Example 8.

IR: (see FIG. 9): $\nu_{max}$ KBr)$^{-1}$: 3350, 1700, 1620, 1540, 1450, 1350 1210, 1060, 1030, 880, 760, 590.

UV: $\lambda_{max}$ (H$_2$O) nm: 213, 277.

EXAMPLE 9

To 20 mg of 1,2,3,4,6-penta-O-galloyl-β-D-glucose, there was added 1 ml of anhydrous pyridine and the resultant mixture was sufficiently stirred in a nitrogen atmosphere with ice-cooling. To the mixture, there was dropwise added 27 mg of chlorosulfonic acid slowly and then the mixture was stirred at room temperature for 12 hours. Water (0.3 ml) was added with ice-cooling, followed by neutralizing it with a saturated sodium hydrogen carbonate aqueous solution and extracting the mixture twice with ethyl acetate to remove pyridine. The resultant water phase was poured into a bag of a membrane filter having a fractional molecular weight of 1,000 (Spectra/pore 6; available from Spectrum Medical Industries Co., Ltd.) to perform dialysis against water for 7 days. The inner solution was lyophilized to thus obtain 20 mg of the sodium salt of sulfuric acid ester of 1,2,3,4,6-penta-O-galloyl-β-D-glucose (PGG-S).

Elemental Analysis: C 29.69; H 2.78; S 7.85 (%).

Figure 10:
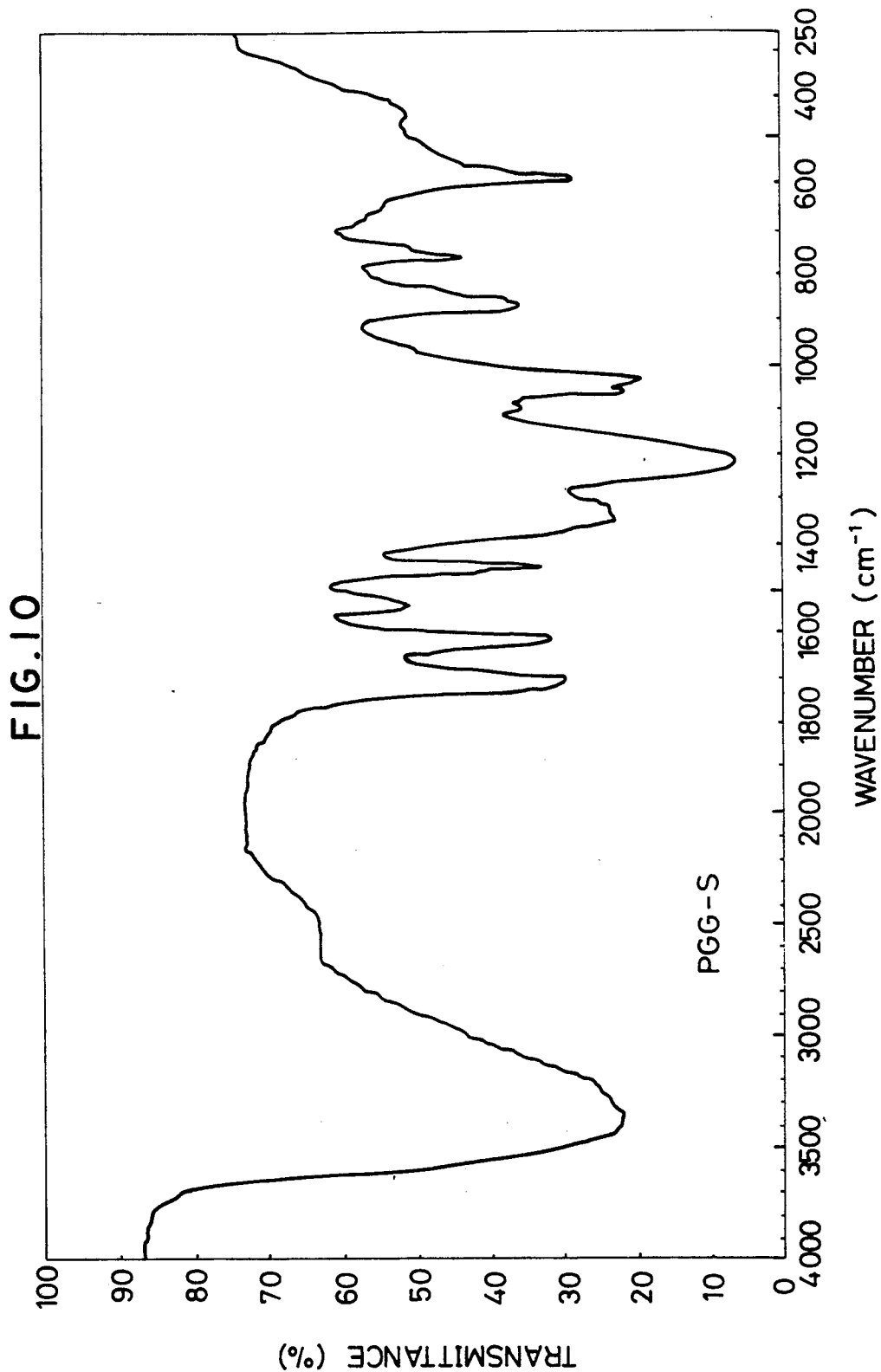
FIG. 10 is a chart of IR absorption spectrum of the compound obtained in Example 9.

IR: (see FIG. 10): $\nu_{max}$ KBr)$^{-1}$: 3400, 1720, 1610, 1540, 1460, 1350 1220, 1020, 870, 770, 590.

UV: $\lambda_{max}$ (H$_2$O) nm: 212, 272.

EXAMPLE 10

To 500 mg of 1,2,3,4,6-penta-O-galloyl-β-D-glucose, there was added 85 ml of anhydrous pyridine and the resultant mixture was sufficiently stirred with ice-cooling. To the mixture, there was dropwise added 19 mg of chlorosulfonic acid slowly and then the mixture was stirred at room temperature for 2 days. Water (50 ml) was added with ice-cooling, followed by neutralizing it with a saturated sodium hydrogen carbonate aqueous solution and extracting the mixture twice with ethyl acetate to remove pyridine. The resultant water phase was poured into a bag of a membrane filter having a fractional molecular weight of 1,000 (Spectra/pore 6; available from Spectrum Medical Industries Co., Ltd.) to perform dialysis against water for 7 days. The inner solution was lyophilized to thus obtain 648 mg of the sodium salt of sulfuric acid ester of 1,2,3,4,6-penta-O-galloyl-β-D-glucose (PGG-S).

Elemental Analysis: C 26.3; H 2.2; S 13.3 (%).

Figure 11:
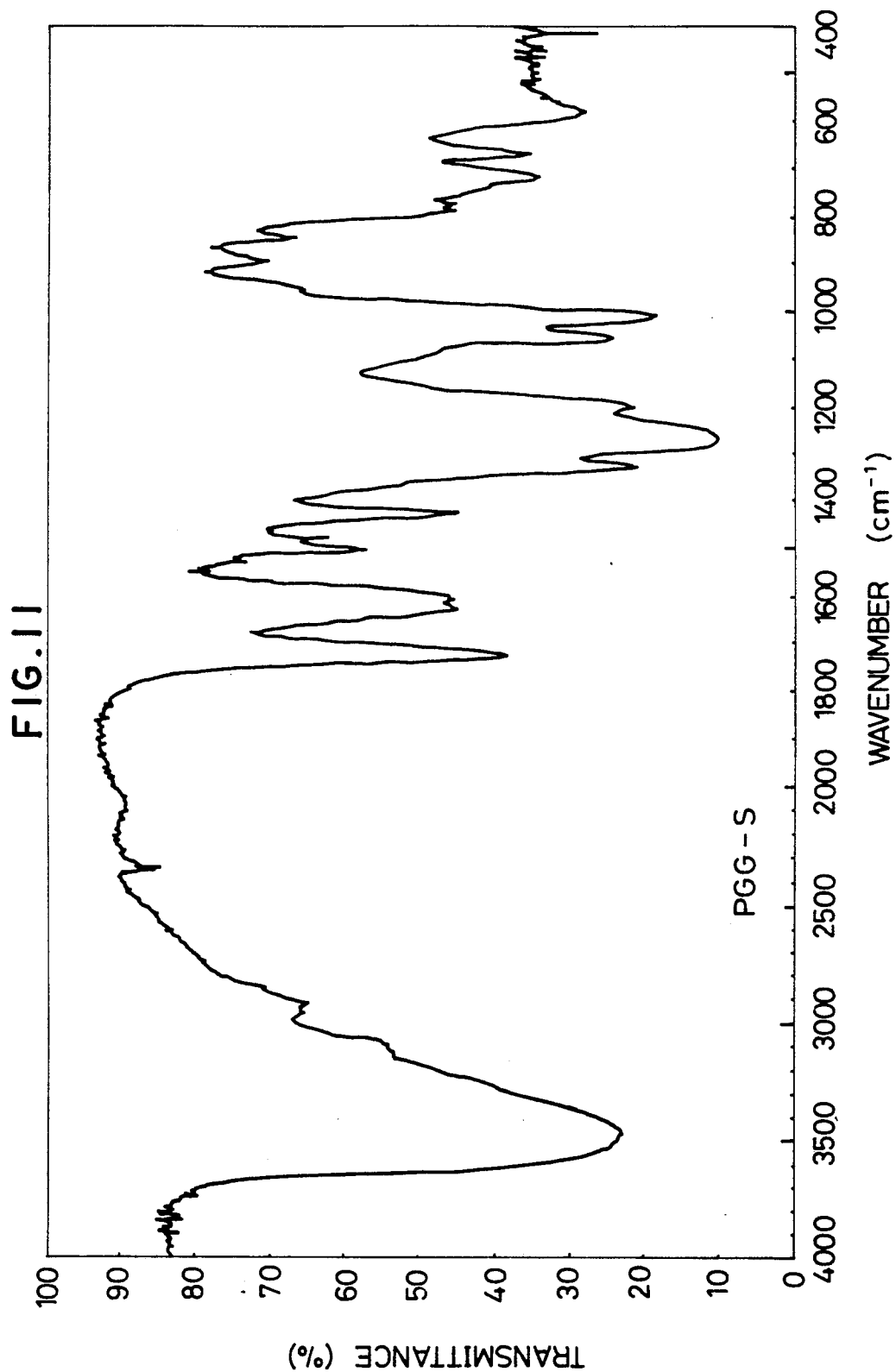
FIG. 11 is a chart of IR absorption spectrum of the compound obtained in Example 10.

IR: (see FIG. 11): $\nu_{max}$ KBr)$^{-1}$: 3466, 1733, 1649, 1638, 1633. 1614. 1509 1434, 1331, 1269, 1202, 1058, 1010, 898 851, 722, 673, 584.

UV: $\lambda_{max}$ (H$_2$O) nm: 209, 258.

REFERENCE EXAMPLE 2

A mixture of 200 mg of tannic acid according to U.S. Pharmacopoeia, 40 ml of 0.05 M acetate buffer solution (pH 5.5) and 80 ml of methanol was reacted at 50° C. for 21 hours. After concentrating the reaction mixture under a reduced pressure into approximately 20 ml, 20 ml of ether was added and then each liquid phase was separated. The water phase was further washed with 20 ml of ethyl acetate and extracted with n-butanol (20 ml). The butanol phase was evaporated to dryness under a reduced pressure to thus obtain 70 mg of the product. The product was fractionated by HPLC (RE 5 $\mu C_{18}$—100 Å, 3.9 mm × 15 cm; linear gradient of A0.1M phosphate buffer solution (pH 4.5) and B 0.1M phosphate buffer solution (pH 4.5): methanol:tetrahydrofuran (13:7:3); flow rate=0.6 ml/minute) and thus fractions containing 3,4-digalloylquinic acid (peak 1) and 3,4,5-Trigalloylquinic acid (peak 2). Each fraction was concentrated under a reduced pressure and extracted with n-butanol. n-Butanol phase was evaporated to dryness in vacuo and the resulting residue was extracted with methanol. The methanol soluble matters were concentrated to dryness and a small of water was added to the residue to dissolve the same and the resultant solution was desalted with a Micro Acilyzer (available from Asahi Chemical Industry Co., Ltd.; under the trade name of AC-110-10 Membrane). The desalted solution was lyophilized to thus obtain 3,4-digalloylquinic acid (19.7 mg) and 3,4,5-trigalloylquinic acid (19.3 mg) as white powder respectively.

3,4-Digalloylquinic Acid

FABMS (Neg): m/z 495 (M-H)$^-$.
$^1$H-NMR $\delta_{ppm}$ (500 MHz; CD$_3$OD): 7.09, 7.00, 5.68, 5.21, 4.43, 2.38, 2.30, 2.12.
IR (KBr) cm$^{-1}$: 3400, 1700, 1620, 1450, 1220, 1040.
UV, $\lambda_{max}$ (MeOH) nm: 215, 276.

3,4,5-Trigalloylquinic Acid

FABMS (Neg): m/z 647 (M-H)$^-$.
$^1$H-NMR $\delta_{ppm}$ (500 MHz; CD$_3$OD): 7.10, 7.03, 7.00, 5.80, 5.75, 5.46, 2.55, 2.46, 2.32, 2.25.
IR (KBr) cm$^{-1}$: 3400, 1703, 1620, 1450, 1218, 1040.
UV, $\lambda_{max}$ (MeOH) nm: 215, 276.

EXAMPLE 11

Chlorosulfonic acid (4.75 g) was dropwise added to a mixture of 125 mg of 3,4-digalloylquinic acid and 21 ml of anhydrous pyridine with stirring and ice-cooling then the mixture was stirred at room temperature for 24 hours. To the mixture, 6 ml of water was added with ice-cooling, followed by neutralizing it with a saturated solution of sodium bicarbonate and extracting twice with ethyl acetate to remove pyridine. After concentrating the aqueous phase, it was poured into a bag of a membrane filter having a fractional molecular weight of 1,000 (Spectra/pore 6; available from Spectrum Medical Industries Co., Ltd.) to perform dialysis against water for 7 days. The inner solution was lyophilized to thus obtain 110 mg of sodium salt of sulfated 3,4-digalloylquinic acid.

Figure 12:
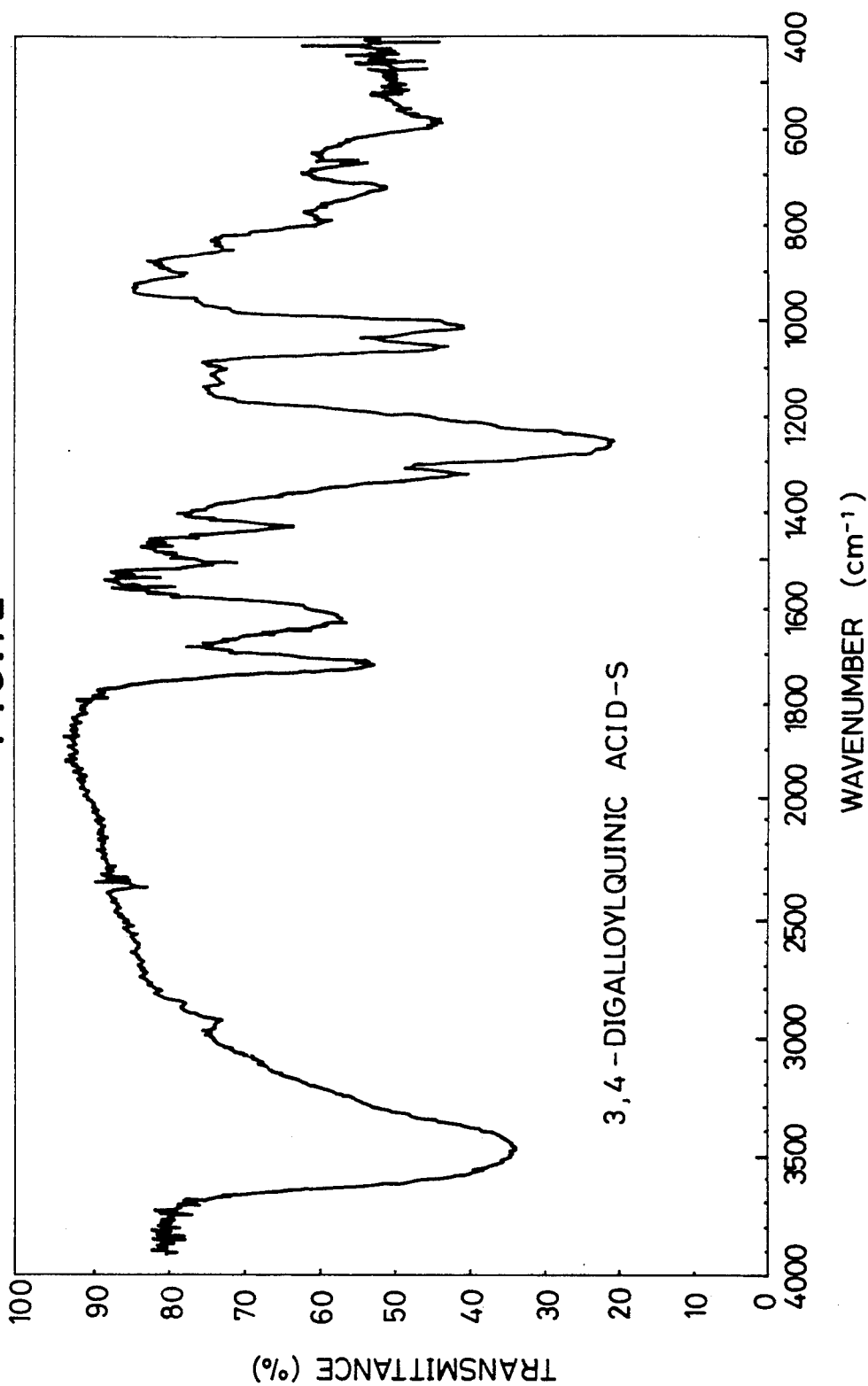
FIG. 12 is a chart of IR absorption spectrum of the compound obtained in Example 11.

Elemental Analysis: C 20.53%; H 2.14%; S 11.18%.
IR (KBr) cm$^{-1}$: 3460, 1730, 1635, 1260, 1060, 1025 (see FIG. 12). UV, $\lambda_{max}$ (H$_2$O) nm: 208, 255.

EXAMPLE 12

The same procedures as used in Example 11 were repeated except that 125 mg of 3,4,5-trigalloylquinic acid was substituted for 125 mg of 3,4-digalloylquinic acid to obtain 149 mg of sodium salt of sulfated 3,4,5-trigalloylquinic acid.

Elemental Analysis: C 22.33%; H 2.07%; S 10.48%.
IR (KBr) cm$^{-1}$: 3470, 1720, 1635, 1260, 1060, 1020 (see FIG. 13).
UV, $\lambda_{max}$ (H$_2$O) nm: 209, 255.

PREPARATION EXAMPLE 1

Manufacture of Injections and Drips

Each sulfated product or its salt as an effective component was mixed with 5 g of powdered dextrose, followed by dispensing the mixture into vials so that 500 mg each of the effective component was contained in each vial while maintaining an aseptic condition, sealing the vials, enclosing an inert gas such as nitrogen or helium gas in each vial and storing these vials at a low temperature in the dark. The drug thus prepared are dispersed in 500 ml of 0.85% physiological saline before use as an intravenous injection. The injection is intravenously injected or administered through drip in an amount ranging from 10 to 500 ml per day depending on the conditions of a patient.

PREPARATION EXAMPLE 2

Manufacture of Injections and Drips

An intravenous injection of a mild case was prepared in the same manner as used in Preparation Example 1 except that each sulfated product or its salt as an effective component was used in an amount of 50 mg. The injection is intravenously injected or administered through drip in an amount ranging from 10 to 500 ml per day depending on the conditions of a patient.

PREPARATION EXAMPLE 3

Injections and Capsules

Each sulfated product or its salt (30 mg) as an effective component was dissolved in a mixture comprising 1 g of purified sesame oil and 100 mg of aluminum stearate gel, followed by dispensing the mixture in a proper container, sealing the container, enclosing an inert gas such as nitrogen or helium gas in the container and storing it at a low temperature in the dark. The pharmaceutical preparation for subcutaneous injection thus prepared is subcutaneously injected once in an amount ranging from 1 to 10 ml per day depending on the conditions of a patient.

Alternatively, 0.5 ml each of the foregoing pharmaceutical preparation is dispensed in capsules to obtain those for oral administration. The capsules are orally administered in an amount ranging from 1 to 10 capsules per day depending on the conditions of a patient.

PREPARATION EXAMPLE 4

Enteric Coated Tablets

In this Example, there were prepared 1,000 each of enteric coated tablets for adult (i) and for infant (ii) comprising the following components and having the following compositions.

|  | (i) (g) | (ii) (g) |
|---|---|---|
| (A) Component |  |  |
| Principal component (sulfated product or salt thereof) | 100 | 50 |
| Lactose | 99.4 | 49.7 |
| Hydroxypropyl cellulose | 0.6 | 0.3 |
| Magnesium stearate | 2.0 | 1.0 |
| (B) Component |  |  |
| Cellulose acetate phthalate | 6.0 | 4.0 |

-continued

|  | (i) (g) | (ii) (g) |
|---|---|---|
| Hydroxypropyl methyl cellulose phthalate | 6.0 | 4.0 |೦

The components of the formulation (A) were mixed sufficiently and the resultant mixture was directly compressed to obtain tablets or the mixture was sufficiently kneaded, formed into granules by passing through a screen or an extrusion granulator, sufficiently dried and then compressed to form tablets.

Then, the formed tablets were coated with the molten formulation (B) to form enteric coated tablets.

When the resulting enteric coated tablets were subjected to the disintegration test in accordance with Japanese Pharmacopoeia using an artificial gastric juice (pH 1.2), the tablets were not disintegrated even after shaking for one hour, but it was disintegrated within 5 to 6 minutes in the disintegration test using and artificial enteric juice (pH 7.5).

PREPARATION EXAMPLE 5

Enteric Coated Granules

Enteric coated granules (1,000 g) were formed from the following components.

|  | Amount (g) |
|---|---|
| (A) Component |  |
| Principal component (sulfated product or its salt) | 100 |
| Lactose | 737 |
| Hydroxypropyl cellulose | 3 |
| (B) Component |  |
| Cellulose acetate phthalate | 80 |
| Hydroxypropyl methyl cellulose phthalate | 80 |

The components of the formulation (A) were sufficiently mixed, formed into granules in an ordinary manner, and the granules were sufficiently dried, sieved and sealed in a bottle or packed in a heat-sealing package. Then the granules were coated with the molten formulation (B) while the granules were maintained in floating and flowing state to form enteric coated granules. When the granules thus obtained were subjected to the disintegration test using a disintegration test device according to Japanese Pharmacopoeia, they were not disintegrated even if they were shaken in an artificial gastric juice of pH 1.2. On the contrary, they were disintegrated in an artificial enteric juice of pH 7.5 within 5 minutes.

PREPARATION EXAMPLE 6

Enteric Coated Capsules

In this Example, there were prepared 1,000 each of enteric coated capsules of adult (i) and for infant (ii) comprising the following components and having, the following compositions.

|  | (i) (g) | (ii) (g) |
|---|---|---|
| (A) Component |  |  |
| Principal component (sulfated product or salt thereof) | 100 | 50 |
| Lactose | 24.6 | 74.4 |
| Hydroxypropyl cellulose | 0.4 | 0.4 |
| (B) Component |  |  |
| Cellulose acetate phthalate | 10 | 10 |
| Hydroxypropyl methyl cellulose phthalate | 10 | 10 |

The same procedures as used in Preparation Example 5 were repeated to form enteric coated granules favorable for capsules and the granules were encapsulated in capsules to obtain enteric coated capsules.

When the capsules thus obtained were subjected to the disintegration test using a disintegration test device according to Japanese Pharmacopoeia, they were not disintegrated or dissolved out therefrom even if they were shaken in an artificial gastric juice of pH 1.2. On the contrary, they were disintegrated or completely dissolved out in an artificial enteric juice of pH 7.5 within 5 minutes.

EXPERIMENT 1

Inhibitory Effect of Drugs on HIV-induced cell damage

In this experiment, there were used human MT4 cells, a human T4-positive cell line carrying adult T-cell leukemia causative virus, HTLV-1 (Gann Monogr.,1982, Vol. 28, pp. 219 -228) and HTLF-IIIB which is one of the HIV strains.

HTLV-IIIB-infected MT-4 cells were inoculated on RPMI 1640 culture mediums containing 10% heat-inactivated fetal calf serum, 100 IU/ml of penicillin and 100 µg/ml of streptomycin, to which tannic acid-S had been added in a variety of concentrations, in a cell number of 300,000/ml and were cultured at 37° C. in a carbon dioxide incubator. After the cultivation for three days, one half of the culture medium was withdrawn and the survival rate and the viable count ($\times 10^4$ /ml) of the MT-4 cells in the medium were determined by a trypan blue dye exclusion test. To the remaining cultured cells, an equivalent amount of RPMI 1640 culture medium each containing the same amount of the drugs were added, the cultivation was further continued for additional 3 days and likewise the survival rate and the viable count were determined. The results obtained are listed in the following Table I.

TABLE I

| Drug Sulfur Content | Tannic acid-S 13.0% | | | |
|---|---|---|---|---|
| Culture Period | 3 days | | 6 days | |
| Drug Concn. (µg/ml) | Viable count ($\times 10^4$/ml) | survival rate (%) | Viable count ($\times 10^4$/ml) | survival rate (%) |
| 400 | 73 | 95 | 12 | 92 |
| 200 | 114 | 92 | 55 | 92 |
| 100 | 131 | 94 | 100 | 94 |
| 50 | 162 | 95 | 151 | 96 |
| 25 | 174 | 91 | 158 | 93 |
| 12 | 167 | 91 | 147 | 89 |
| 6 | 157 | 97 | 158 | 93 |
| 3 | 166 | 92 | 32 | 38 |
| 0 | 33 | 56 | 1 | 8 |

EXPERIMENT 2

Inhibitory Effect of Drug on Expression of HIV-specific Antigen

After drying the cells cultured in Experiment 1 on a slide glass, they were fixed with methanol for 3 minutes and treated with human anti-HIV-III positive serum (IF antibody titer $\times 4096$) which was diluted 1/1,000 time at 37° C. for 30 minutes. Thereafter, it was washed with phosphate-buffered saline (PBS) for 15 minutes and treated with an anti-human IgG conjugated with fluorescein-isothiocyanate at 37° C. for 30 minutes. It was again washed with PBS and then the number of fluorescent cells, more specifically expressed HIV-specific virus antigen proteins were determined with a fluorescence microscope. The results observed are summarized in the following Table II. "%" is a ratio of the number of fluorescent ray emitting cells to the number of total cells.

TABLE II

| Drug Sulfur Content (%) | Tannic acid-S 13.0 | |
|---|---|---|
| Culture Period | 3 days | 6 days |
| Concn. of Drug (μg/ml) | Ratio (%) | |
| 400 | 0 | 0 |
| 200 | 0 | <1 |
| 100 | 0 | <1 |
| 50 | 0 | <1 |
| 25 | <1 | <1 |
| 12 | <1 | <1 |
| 6 | <1 | <1 |
| 3 | <1 | 90 |
| 0 | 62 | 94 |

EXPERIMENT 3

The inhibitory effect of ellagic acid sulfate was determined as in Experiment 1. The results obtained are listed in Table III given below.

TABLE III

| Drug Sulfur Content (%) | Ellagic acid-S 12.0 | |
|---|---|---|
| Culture Period | 3 days | 6 days |
| Concn. of Drug (μg/ml) | Viable count (× 10⁴/ml) | |
| 400 | 73 (82) | 47 (89) |
| 200 | 83 (87) | 86 (83) |
| 100 | 81 (84) | 103 (78) |
| 50 | 74 (82) | 23 (43) |
| 0 | 60 (81) | 1 (5.6) |

Note:
The numerals given in parentheses represent survival rate (%).

EXPERIMENT 4

The inhibitory effect of ellagic acid sulfate was determined as in Experiment 2. The results obtained are listed in Table IV given below.

TABLE IV

| Drug Sulfur Content (%) | Ellagic acid-S 12.0 | |
|---|---|---|
| Culture Period | 3 days | 6 days |
| Concn. of Drug (μg/ml) | Ratio (%) | |
| 400 | 0 | <1 |
| 200 | <1 | <1 |
| 100 | <1 | 6.4 |
| 50 | <1 | 90 |
| 0 | 33.3 | 89.7 |

EXPERIMENT 5

The inhibitory effect of epicatechin sulfate was determined as in Experiment 1. The results obtained are listed in Table V given below.

TABLE V

| Drug Sulfur Content (%) | Epicatechin-S 16.8 | |
|---|---|---|
| Culture Period | 3 days | 6 days |
| Concn. of Drug (μg/ml) | Viable count (× 10⁴/ml) | |
| 400 | 91 (85) | 133 (91) |
| 200 | 89 (86) | 122 (91) |
| 100 | 99 (87) | 110 (92) |
| 50 | 94 (95) | 45 (63) |
| 0 | 60 (81) | 1 (5.6) |

Note:
The numerals given in parentheses represent survival rate.

EXPERIMENT 6

The inhibitory effect of epicatechin sulfate was determined as in Experiment 2. The results obtained are listed in Table VI given below.

TABLE VI

| Drug Sulfur Content (%) | Epicatechin-S 16.8 | |
|---|---|---|
| Culture Period | 3 days | 6 days |
| Concn. of Drug (μg/ml) | Ratio (%) | |
| 400 | <1 | <1 |
| 200 | <1 | <1 |
| 100 | <1 | <1 |
| 50 | <1 | 90 |
| 0 | 33.3 | 90 |

EXPERIMENT 7

The inhibitory effect of sulfuric acid ester of epigallocatechin gallate was determined as in Experiment 1. The results obtained are listed in Table VII given below.

TABLE VII

| Drug Sulfur Content (%) | Epigallocatechin Gallate-S 15.3 | |
|---|---|---|
| Culture Period | 3 days | 6 days |
| Concn. of Drug (μg/ml) | Viable count (× 10⁴/ml) | |
| 400 | 72 (82) | 50 (86) |
| 200 | 81 (89) | 75 (87) |
| 100 | 84 (83) | 125 (95) |
| 50 | 83 (85) | 130 (92) |
| 0 | 60 (81) | 1 (5.6) |

Note:
The numerals given in parentheses represent survival rate.

EXPERIMENT 8

The inhibitory effect of sulfuric acid ester of epigallocatechin gallate was determined as in Experiment 2. The results obtained are listed in Table VIII given below.

TABLE VIII

| Drug Sulfur Content (%) | Epigallocatechin Gallate-S 15.3 | |
|---|---|---|
| Culture Period | 3 days | 6 days |
| Concn. of Drug (μg/ml) | Ratio (%) | |
| 400 | <1 | <1 |
| 200 | <1 | <1 |
| 100 | <1 | <1 |
| 50 | <1 | <1 |
| 0 | 33.3 | 90 |

EXPERIMENT 9

Inhibitory Effect on Giant Cell Formation by Mixed Cell Cultivation of MOLT-4 · MOLT-4/HIV H TL VI II B This experiment was performed by the recently developed method of Yamamoto et al. (see Yamamoto et al., Virology, 1988, 164, p. 542; and J. Clinical Microbiology, 1988, 26, p. 1229).

MOLT-4 cells which are HTLV-I negative human T cell strain, and MOLT-4/HIV$_{HT LV II IB}$ cells which are persistently HIV-infected cells are separately cultured in a RPMI 1640 culture medium supplemented with 10% fetal calf serum to a cell density of $5 \times 10^5$/ml respectively, these were mixed in a ratio of 1:1 and the drug was added thereto.

The mixed culture medium was cultured at 37° C. for 24 hours in a carbon dioxide incubator and the distribution of cell size was determined by a Cell Multisizer (available from Coulter Electronics, Ltd., Luton, England). The results obtained are summarized in the following Table IX.

In Table IX, the rate of cell having a size of not less than 20 μm is expressed by "%". If MOLT-4 cells and MOLT-4/HIV$_{HT LV II IB}$ cells are separately cultured, the rates are 4.5 and 3.3% respectively, but it increased up to 18.5% when they are co-cultured. When tannic acid-S was added to the mixed culture medium in a concentration of 5 μg/ml, the rate was reduced to 8.2%. This clearly shows that tannic acid-S has inhibitory effect on giant cell formation. The rates, 13.9%, 9.5% and 5.6%, were achieved by the use of epicatechin-S (200 μg/ml), ellagic acid-S (200 μg/ml) and epigallocatechin gallate-S (100 μg/ml) respectively.

TABLE IX

| Drug | | Drug Concn. (μg/ml) | Rate of Giant Cell (%) |
|---|---|---|---|
| Control: | only MOLT-4 | 0 | 4.5 |
| | only MOLT-4/ HIV$_{HT LV II IB}$ | 0 | 3.3 |
| | Coculture | 0 | 18.5 |
| Tannic acid-S | | 100 | 6.8 |
| | | 50 | 7.1 |
| | | 10 | 6.1 |
| | | 5 | 8.2 |
| Epicatechin-S | | 200 | 13.9 |
| | | 100 | 15.1 |
| | | 50 | 14.0 |
| | | 25 | 14.2 |
| Ellagic acid-S | | 200 | 9.5 |
| | | 100 | 13.0 |
| | | 50 | 17.0 |
| | | 25 | 15.1 |
| Epigallocatechin gallate-S | | 200 | 0.4 |
| | | 100 | 5.6 |
| | | 50 | 17.5 |
| | | 25 | 13.8 |

EXPERIMENT 10

Determination of RTase Inhibitory Effect

According to the method disclosed in Journal of Biological Chemistry, 1987, 262, p. 2187, the RTase inhibitory effect of the compounds of this invention is determined as follows:

More specifically, the compound of the present invention was added, in various amount, to a reaction solution which comprised 80 mM of Tris buffer solution (pH 8), 6 mM of magnesium chloride, 80 mM of potassium chloride, 10 mM of dithiothreitol, 20 μg/ml of polyadenylic acid, 0.02 μg/ml of oligodeoxy thymidine, 20 μM of tritium-labeled deoxythymidine-triphosphate and avian myeloblastosis virus RTase so that the total volume of the resultant solution was equal to 100 μl. After the reaction solution was incubated at 37° C. for 40 minutes, 100 μl of an ice-cooled 10% trichloroacetic acid solution was added to the solution to stop the reaction.

The reaction solution was filtered through a glass filter (Whatmann GF/C) and washed with a 10% trichloroacetic acid solution and then with ethanol. Thereafter, the glass filter was dried and examined by liquid scintillation counter.

The RTase inhibitory effect of the compounds (the effective component) of the present invention determined by the aforementioned method are listed in Table X given below (in Table X, the effect is expressed in $IC_{50}$).

TABLE X

| Compound Examined | RTase Inhibitory Effect ($IC_{50}$ μg/ml) |
|---|---|
| Example 2 | 0.22 |
| Control*[1] | 44 |
| Example 7 | 0.45 |
| Example 9 | <0.096 |
| Control*[2] | >60 |
| Example 12 | 9.2 |
| Control*[3] | >100 |

*[1]Tannic Acid according to Japanese Pharmacopoeia (available from IWAKI PHARMACEUTICALS CO., LTD.)
*[2]Pentagalloylglucose.
*[3]3,4,5-Trigalloylquinic acid

Test on Toxicity (A) Influence on the Proliferation of T Cells

As in Experiment 1, there was observed the influence of the compounds (drugs) of the present invention on the proliferation of HTLV-IIIB-non-infected MT-4 cells. The results thus observed are listed on the following Tables XI to XIV. The numerical values in these Tables mean viable count ($\times 10^4$/ml) and those in parentheses mean survival rates.

TABLE XI

| Drug Sulfur Content (%) | Tannic acid-S 13.0 | |
|---|---|---|
| Culture Period | 3 days | 6 days |
| Drug Concn. (μg/ml) | Viable count ($\times 10^4$/ml) | |
| 400 | 89 | 5 |
| 200 | 108 | 72 |
| 100 | 148 | 107 |
| 50 | 196 | 149 |
| 25 | 167 | 169 |
| 12 | 183 | 165 |
| 6 | 178 | 154 |
| 3 | 168 | 152 |
| 0 | 200 | 147 |

TABLE XII

| Drug Sulfur Content (%) | Ellagic acid-S 12.0 | |
|---|---|---|
| Culture Period | 3 days | 6 days |
| Drug Concn. (μg/ml) | Viable count ($\times 10^4$/ml) | |
| 400 | 81 (84) | 70 (82) |
| 200 | 99 (83) | 104 (85) |
| 100 | 99 (87) | 109 (83) |
| 50 | 70 (84) | 137 (89) |
| 0 | 117 (92) | 142 (94) |

TABLE XIII

| Drug | Epicatechin-S | |
|---|---|---|
| Sulfur Content (%) | 16.8 | |
| Culture Period | 3 days | 6 days |
| Drug Concn. (μg/ml) | Viable count (× 10⁴/ml) | |
| 400 | 118 (86) | 137 (92) |
| 200 | 111 (83) | 133 (92) |
| 100 | 110 (86) | 147 (93) |
| 50 | 114 (91) | 138 (85) |
| 0 | 117 (92) | 142 (94) |

TABLE XIV

| Drug | Epigallocatechin gallate-S | |
|---|---|---|
| Sulfur Content (%) | 15.3 | |
| Culture Period | 3 days | 6 days |
| Drug Concn. (μg/ml) | Viable count (× 10⁴/ml) | |
| 400 | 96 (89) | 53 (95) |
| 200 | 90 (91) | 95 (92) |
| 100 | 114 (85) | 37 (91) |
| 50 | 106 (88) | 40 (92) |
| 0 | 117 (92) | 42 (94) |

As seen from the results listed in the foregoing Tables, the influence of the compounds of the present invention on the proliferation of T cells is very weak in all cases. Moreover, it is also found that the higher the sulfur content is, the weaker the influence of the compounds effects on the proliferation of T cells.

On the other hand, it has been reported that AZT shows, at a concentration of the order of 5 $\mu$M (1.3 $\mu$g/ml), suppression of the proliferation of T cells in the order of 25 to 50% compared with the control (see Hideki Nakashima, Gann, 1987, 78, p. 583).

In addition, these compounds of the present invention do not show any inhibitory effect on the proliferation of culture cells such as Ehrlich-Littre Ascites Carcinoma Strain E cells and mouse leukemia cells L 1210 at a concentration of the order of 100 $\mu$g/ml.

It is known that some polysaccharides such as dextran sulfate and heparin cannot be used in the treatment of patients suffering from hemophilia since they show blood coagulation inhibitory effect or the like (see the morning edition of the NIPPON KEIZAI, 1988, Dec. 6).

What is claimed is:

1. A sulfated tannin compound selected from the group consisting of pentagalloylglucose, a sulfated digalloylquinic acid and a sulfated trigalloylquinic acid represented by the following formula (I) or (II):

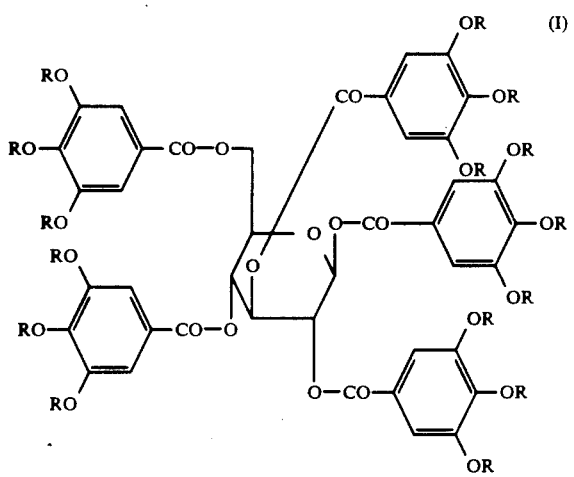

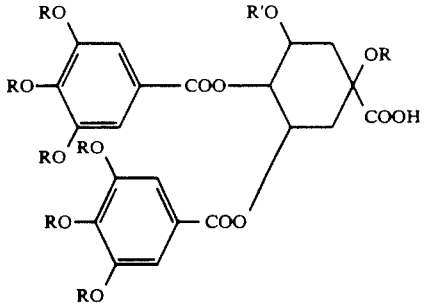

wherein R' represents —H, —SO₃H or a group represented by the following formula:

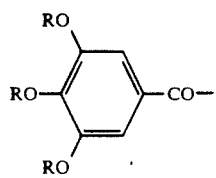

and R represents —H or —SO₃H, except for where all of the substituents R represent —H, or a salt thereof.

2. The compound of claim 1 wherein the average degree of sulfation of the sulfated compound or the salt thereof ranges from 10 to 70%.

3. A sulfated tannin compound wherein the tannin is a member selected from the group consisting of tannic acid, ellagic acid, epicatechin, epigallocatechin gallate, pentagalloylglucose, digalloylquinic acid and trigalloylquinic acid.

4. A pharmaceutical composition useful as an antiviral agent comprised of an antiviral-effective amount of the sulfated tannin compound or salt thereof of claim 3 and a pharmaceutically acceptable carrier.

5. The antiviral agent pharmaceutical composition of claim 4 wherein the sulfated tannin or the salt thereof is a member selected from the group consisting of a sulfated pentagalloylglucose, a sulfated digalloylquinic acid and a sulfated trigalloylquinic acid represented by the following formula (I) or (II):

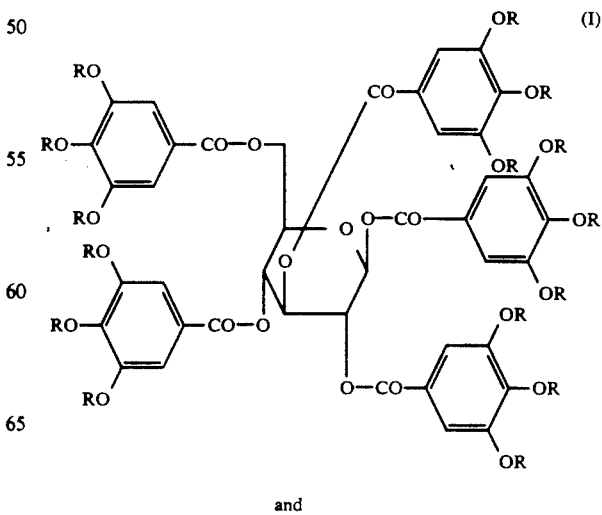

-continued

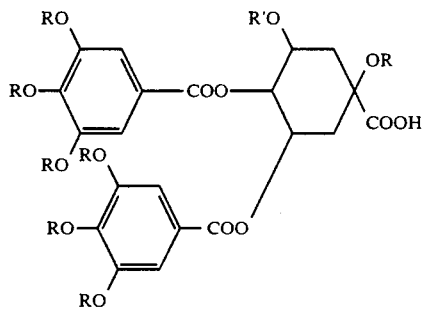

wherein R' represents —H, —SO₃H or a group represented by the following formula:

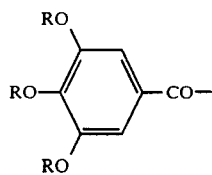

(II)

and R represents —H or —SO₃H, except for where all of the substituents R represent —H, or a salt thereof.

6. The antiviral agent of claim 5 wherein the average degree of sulfation of the sulfated compound or the salt thereof ranges from 10 to 70%.

7. A sulfated tannin compound wherein the tannin is a sodium or potassium salt of a member selected from the group consisting of tannic acid, ellagic acid, epicatechin, epigallocatechin gallate, pentagalloylglucose, digalloylquinic acid and trigalloylquinic acid.

8. A pharmaceutical composition comprised of a therapeutically-effective amount of the sulfated tannin compound of claim 7 and a pharmaceutically acceptable carrier.

9. The pharmaceutical composition of claim 8, wherein the average degree of sulfation of the sulfated tannin compound ranges from 10 to 70%.

* * * * *